(12) United States Patent
Hayes et al.

(10) Patent No.: US 8,193,112 B2
(45) Date of Patent: Jun. 5, 2012

(54) CATALYSTS FOR THE POLYMERIZATION OF CYCLIC ESTERS

(75) Inventors: Paul G. Hayes, Lethbridge (CA); Craig Wheaton, Lethbridge (CA)

(73) Assignee: University of Lethbridge, Lethbridge (CA)

( * ) Notice: Subject to any disclaimer, the term of this patent is extended or adjusted under 35 U.S.C. 154(b) by 99 days.

(21) Appl. No.: 12/624,936

(22) Filed: Nov. 24, 2009

(65) Prior Publication Data

US 2010/0130753 A1    May 27, 2010

Related U.S. Application Data

(60) Provisional application No. 61/117,363, filed on Nov. 24, 2008.

(51) Int. Cl.
*C07D 313/04* (2006.01)
*C07D 319/10* (2006.01)
*B01J 31/12* (2006.01)
*B01J 31/18* (2006.01)

(52) U.S. Cl. ........ 502/155; 502/167; 502/133; 502/183; 549/266; 549/274

(58) Field of Classification Search ................ None
See application file for complete search history.

(56) References Cited

U.S. PATENT DOCUMENTS

| | | | |
|---|---|---|---|
| 5,204,121 A | 4/1993 | Bücheler |
| 5,225,129 A | 7/1993 | Van Den Berg |
| 5,235,031 A | 8/1993 | Drysdale |
| 6,469,133 B2 | 10/2002 | Baker |

FOREIGN PATENT DOCUMENTS
WO    WO2007/148136 A2    12/2007

OTHER PUBLICATIONS

Hannant et al. "Synthesis and catalytic activity of three-coordinate zinc cations" published Oct. 2002.*
Venkateswaran et al. Eur. J. Inorg. Chem., 2007, 1930-1938, Published Online: Mar. 16, 2007.*
SciFinder search history.*
Wheaton et al, "Cationic Organozinc Complexes of a Bis(phosphinimine) Pincer Ligand: Synthesis and Structural Studies", Dalton Transactions, 2010, pp. 3861-3869, vol. 39(16).
Ireland et al., "Cationic Organomagnesium Complexes as Highly Active Initiators for the Ring-Opening Polymerization of ε-Caprolactone", Organometallics, 2010, pp. 1079-1084, vol. 29(5).
Wheaton et al., "Zinc Complexes of Neutral Phosphinimine Ligands: Toward Lactide Polymerization Catalysts" (Poster Presentation), 91st Canadian Society for Chemistry Conference, May 2008, Abs. No. 246, Edmonton, AB, Canada.
Hayes et al., "Alkaline Earth Metal Complexes Supported by Tridentate Ancillary Ligands: Toward Novel Lactide Polymerization Catalysts" (Invited Presentation), 235th ACS National Meeting, Apr. 6, 2008, Abs. No. INOR98, New Orleans, LA, USA.

(Continued)

*Primary Examiner* — Melvin C Mayes
*Assistant Examiner* — Yun Qian
(74) *Attorney, Agent, or Firm* — Bereskin & Parr LLP/S.E.N.C.R.L., s.r.l.; Patricia Folkins

(57) ABSTRACT

The present disclosure relates to cationic divalent metal catalysts useful for the polymerization of cyclic esters, methods for their preparation and uses thereof.

27 Claims, 12 Drawing Sheets

OTHER PUBLICATIONS

Wheaton et al., "Neutral and Zinc Complexes of a Neutral Phosphinimine Ligand: Progress Toward Lactide Polymerization Catalysts" (Poster Presentation), 2nd Annual Chinook Symposium for Chemistry and Biochemistry, Oct. 2008, Abs. No. 27, Lethbridge, AB, Canada.

Hayes et al., "New Ancillary Ligands for Organometallic Chemistry: Toward the Development of Novel Structures, Reactivity and Catalysis", (Invited Lecture and Recruitment Session), Cape Breton University, Jul. 2008, Sydney, NS, Canada.

Wheaton et al, "Activated Zinc Complexes Supported by a Neutral, Phosphinimine-Containing Ligand: Synthesis and Efficacy for the Polymerization of Lactide", Organometallics, 2009, pp. 1282-1285, vol. 28(5).

Williams et al., "A Highly Active Zinc Catalyst for the Controlled Polymerization of Lactide", J. Am. Chem. Soc., Aug. 21, 2003, pp. 11350-11359, vol. 125.

Jensen et al., "Stereoselective Polymerization of D,L-Lactide Using N-Heterocylic Carbene Based Compounds", Chem. Commun., Sep. 8, 2004, pp. 2504-2505.

Jeong et al., "Synthesis of Polylactide Using a Zinc Complex Containing (S)-N-ethyl-N-phenyl-2-pyrrolidinemethanamine", Polyhedron, Oct. 30, 2007, pp. 319-324, vol. 27.

Börner et al., "[Bis(guanidine)]zinc Complexes and Their Application in Lactide Polymerisation", Eur. J. Inorg. Chem., 2007, pp. 5645-5651.

Dagorne et al., "Well-defined Cationic Alkyl- and Alkoxide-Aluminum Complexes and Their Reactivity with ϵ-Caprolactone and Lactides", Chem. Eur. J., 2007, pp. 3202-3217, vol. 13.

Sarazin et al., "Novel Zinc and Magnesium Alkyl and Amido Cations for Ring-Opening Polymerization Reactions", Organometallics, May 28, 2004, pp. 3296-3302, vol. 23.

Alonso-Moreno et al., "Discrete Heteroscorpionate Lithium and Zinc Alkyl Complexes. Synthesis, Structural Studies, and ROP of Cyclic Esters", Organometallics, 2008, pp. 1310-1321, vol. 27.

O'Keefe et al., "Polymerization of Lactide and Related Cyclic Esters by Discrete Metal Complexes", J. Chem. Soc., Dalton Trans., Jul. 16, 2001, pp. 2215-2224.

Hill et al., "Synthesis of C2 and Cs Symmetric Zinc Complexes Supported by Bis(phosphinimino)methyl Ligands and their use in Ring Opening Polymerisation Catalysis", J. Chem. Soc., Dalton Trans., Nov. 18, 2002, pp. 4694-4702.

Cheng et al., "Single-Site Catalysts for Ring-Opening Polymerization: Synthesis of Heterotactic Poly(lactic acid) from rac-Lactide:", J. Am. Chem. Soc., 1999, pp. 11583-11584, vol. 121.

Chisholm et al., "Molecular Design of Single-Site Metal Alkoxide Catalyst Precursors for Ring-Opening Polymerization Reactions Leading to Polyoxygenates. 1. Polylactide Formation by Achiral and Chiral Magnesium and Zinc Alkoxides, ($\eta$3-L)MOR, Where L = Trispyrazolyl- and Trisindazolylborate Ligands", J. Am. Chem. Soc., 2000, pp. 11845-11854, vol. 122.

Lian et al., "Aluminum and Zinc Complexes Based on an Amino-Bis(pyrazolyl) Ligand: Synthesis, Structures, and Use in MMA and Lactide Polymerization", Inorganic Chemistry, Nov. 23, 2006, pp. 328-340, vol. 46.

Platel et al., "Biocompatible Initiators for Lactide Polymerization", Polymer Reviews, Jan. 1, 2008, pp. 11-63, vol. 48(1).

Chen et al., "Ring-Opening Polymerization of Lactides Initiated by Zinc Alkoxides Derived from NNO-Tridentate Ligands", Macromolecules, May 2, 2006, pp. 3745-3752, vol. 39.

Wu et al., Coord. Chem. Rev., 2006, pp. 602-626, vol. 250.

Samantaray, K.L et al., Eur. J. Inorg. Chem. 2006, 2975-2984.

Kranenburg M, et al., Organometallics 1995, 14, 3081-3089.

Murata S, et al., Org. Chem. 1997, 62, 3055-3061.

Sheldrick, G.M., Acta. Cryst. 2008, A64, 112-112.

\* cited by examiner

CATALYSTS FOR THE POLYMERIZATION OF CYCLIC ESTERS

FIELD

The present disclosure relates to new catalysts for the polymerization of cyclic esters, including lactides and cyclic lactones, methods for their preparation and uses thereof.

BACKGROUND

Polylactones have received growing attention in recent years as an environmentally friendly, potentially carbon neutral alternative to conventional polyolefins. Consequently, the development of new single-site metal catalysts for the ring-opening polymerization of lactones has seen tremendous growth over the past decade.[1] Several important families of single-site zinc catalysts have been developed which exhibit high polymerization activity.[2] However, these studies have predominantly employed neutral catalyst species supported by anionic ancillary ligands. A handful of recent studies have considered the use of neutral ligands,[3] though very few cationic species have been successfully applied to lactide polymerization.[2e,4]

SUMMARY OF THE DISCLOSURE

While there are a variety of homogeneous (soluble) catalysts which are active for the polymerization of lactones, the present approach is unique in a number of ways. Firstly, new ancillary ligands (molecular scaffold which binds to the metal centre and ultimately controls the reactivity and selectivity of the catalyst) have been designed and synthesized. The vast majority (>99%) of ligands in currently available systems are anionic (possess a "−1" charge). The downfall of monoanionic ligands is that if they are to be used in conjunction with inexpensive, non-toxic, divalent metals, such as magnesium, zinc, or calcium, then only one valence or reactive M-R (R=alkyl, amido or alkoxide) functionality remains for subsequent chemistry (general catalyst structure=LMR (L=ancillary ligand, M=divalent metal)). The present ligand system, however, is neutral, thereby affording a general precursor catalyst structure of $LMR_2$. Thus, with two reactive M-R bonds, a much greater range of chemical possibilities exists. In particular, it has been established that reaction with Lewis or Brønsted acids affords an electronically and sterically unsaturated (inherently more reactive complex) catalyst species of form [LMR]+. The general catalyst structure dictated by monoanionic ligands precludes this activation strategy because the resultant species ([LM]+) lack the necessary M-R bond required for substrate insertion, and hence, polymerization by a coordination/insertion mechanism.

Accordingly, the present disclosure includes a catalyst for cyclic lactone polymerization of the formula I:

$$[L-M-R^1]^+X^- \quad (I)$$

wherein

L is a neutral ancillary ligand;

M is a divalent metal suitable for cyclic lactone polymerization;

$R^1$ is selected from halo, $R^a$, $OR^a$, $C(O)R^a$, $C(O)OR^a$, $OC(O)R^a$, $C(O)NR^aR^b$ and $NR^aR^b$, wherein $R^a$ and $R^b$ are simultaneously or independently selected from H, $C_{1-10}$alkyl, fluoro-substituted $C_{1-10}$alkyl and $C_{6-14}$aryl wherein $C_{6-14}$aryl is unsubstituted or substituted with one or more substituents independently selected from halo, $C_{1-6}$alkyl, $NR^aR^b$, $OR^a$ and phenyl; and X is a suitable non- or weakly-coordinating anion.

The present disclosure also includes methods of preparing the catalysts of formula I. Accordingly, in one embodiment, the catalysts of formula I are prepared by reacting a compound of formula II:

$$LMR^1R^2 \quad (II)$$

wherein

L is a neutral ancillary ligand;

M is a divalent metal suitable for cyclic lactone polymerization; and $R^1$ and $R^2$ are independently selected from halo, $R^a$, $OR^a$, $C(O)R^a$, $C(O)OR^a$, $OC(O)R^a$, $C(O)NR^aR^b$ and $NR^aR^b$, wherein $R^a$ and $R^b$ are simultaneously or independently selected from H, $C_{1-10}$alkyl, fluoro-substituted $C_{1-10}$alkyl and $C_{6-14}$aryl, wherein $C_{6-14}$aryl is unsubstituted or substituted with one or more substituents independently selected from halo, $C_{1-6}$alkyl, $NR^aR^b$, $OR^a$ and phenyl, with a suitable Brønsted acid or Lewis Acid under conditions for the formation of the compound of formula I.

In a further embodiment, an alternate method for generating the catalysts of the present disclosure has been developed. As opposed to adding a Lewis or Brønsted acid to the neutral metal complexes of formula II ($LMR^1R^2$), it has been shown that a Brønsted acid can be reacted directly with the neutral ancillary ligand to produce a positively charged species ([HL]+). This compound can be isolated as a well behaved solid, and upon reaction with the appropriate metal precursor (e.g. $MR^1R^2$), generates the desired cationic complex of formula I in one step. It has been established that this reaction strategy is general, as different acids can be used to produce [HL]+. This is notable because it dramatically increases the economic viability of large scale production of such catalysts.

Accordingly, the present disclosure includes a process for the preparation of a catalyst of formula I comprising:

(a) reacting a neutral ancillary ligand (L) with a suitable Brønsted acid under conditions to form a protonated ligand of the formula III:

$$[LH]^+X^- \quad (III)$$

wherein L is a neutral ancillary ligand; and

X is a suitable non- or weakly-coordinating anion; and (b) reacting the compound of formula III with a compound of the formula IV:

$$MR^1R^2 \quad (IV)$$

wherein M is a divalent metal suitable for cyclic lactone polymerization; and $R^1$ and $R^2$ are independently selected from $R^1$ is selected from halo, $R^a$, $OR^a$, $C(O)R^a$, $C(O)OR^a$, $OC(O)R^a$, $C(O)NR^aR^b$ and $NR^aR^b$, wherein $R^a$ and $R^b$ are simultaneously or independently selected from H, fluoro-substituted $C_{1-10}$alkyl and $C_{6-14}$aryl, wherein $C_{6-14}$aryl is unsubstituted or substituted with one or more substituents independently selected from halo, $C_{1-6}$alkyl, $NR^aR^b$, $OR^a$ and phenyl, under conditions for the formation of the compound of formula I.

In an embodiment of the disclosure, the neutral ancillary ligand is chiral.

In another embodiment of the disclosure, the neutral ancillary ligand is a compound of the formula (V)

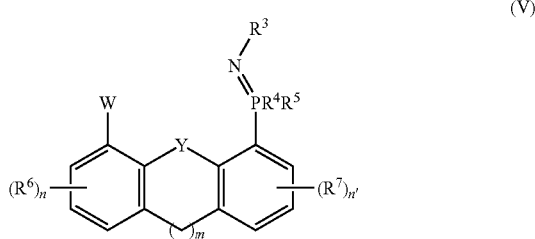

(V)

wherein

Y is O or S;

R³ is selected from C$_{1-20}$alkyl, C$_{3-20}$cycloalkyl, C$_{6-14}$aryl and Si(R$^c$)$_3$, said latter 4 groups being optionally substituted with one or more substituents independently selected from C$_{1-6}$alkyl, fluoro-substituted C$_{1-6}$alkyl, phenyl, phenyl substituted with one to five C$_{1-6}$alkyl, and halo, wherein R$^c$ is selected from C$_{1-20}$alkyl, fluoro-substituted C$_{1-20}$alkyl, C$_{3-20}$cycloalkyl and C$_{6-14}$aryl;

R⁴ and R⁵ are simultaneously or independently selected from C$_{1-20}$alkyl, C$_{3-20}$cycloalkyl and C$_{6-14}$aryl, said latter 3 groups being optionally substituted with one or more substituents independently selected from C$_{1-6}$alkyl, fluoro-substituted C$_{1-6}$alkyl and halo;

R⁶ and R⁷ are simultaneously or independently selected from C$_{1-6}$alkyl, fluoro-substituted C$_{1-6}$alkyl, C$_{6-14}$aryl and halo;

W is a H, a chiral group or —P(R⁸R⁹)=N—R¹⁰, wherein R⁸, R⁹ and R¹⁰ are as defined for R⁴, R⁵ and R³, respectively;

m is 0, 1 or 2; and n and n' are simultaneously or independently 0, 1, 2 or 3.

A notable advantage of the ligand of formula V is that it has been specifically designed so that installation of a chiral group proximal to the metal centre is relatively easy. The installation of a chiral group is desirable as chiral catalysts often possess the ability to stereoselectively polymerize a cyclic lactone. The stereochemistry of the polymer (the way in which the individual monomers link together) ultimately controls the macroscopic properties (e.g. rate of biodegradation, rate of absorption in a living system, processability, hardness, flexibility, etc.) of the material. For example, there are currently no catalyst systems which efficiently, and predictably, control all aspects of polylactide stereochemistry. One of the main reasons for this is due to the fact that the few chiral catalysts which do exist generally have the chirality installed at a point distal to the metal centre. As a result, the degree of chiral induction is minimal. The present ligand of formula V is desirable because it allows the installation of the chiral functional group much closer to the metal centre, thus providing greater control over the stereochemistry of the polymer. Greater control of the polymer microstructure will allow one to systematically fine-tune the physical properties of the material to match the requirements of a given application.

In another embodiment of the disclosure, the cationic divalent metal catalysts of formula I are used in methods for the polymerization of cyclic lactones, for example lactide, glycolide, ε-caprolactone, dioxanone, 1,4-dioxane-2,3-dione, beta-propiolactone, tetramethyl glycolide, beta-butyrolactone, gammabutyrolactone or pivalolactone, or cyclic carbonates such as trimethylene carbonate, 2,2-dimethyl trimethylene carbonate and the like.

The present disclosure allows for the facile preparation of inexpensive and non-toxic cationic divalent metal catalysts, which are very reactive for catalyzing the polymerization of cyclic esters.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

The present disclosure will now be described in greater detail with reference to the following drawings in which:

FIG. 4 shows the X-ray crystal structure of compound 6a;

FIG. 10 shows the X-ray crystal structure of compound 9a;

DETAILED DESCRIPTION OF THE DISCLOSURE

Definitions

Figure 1:
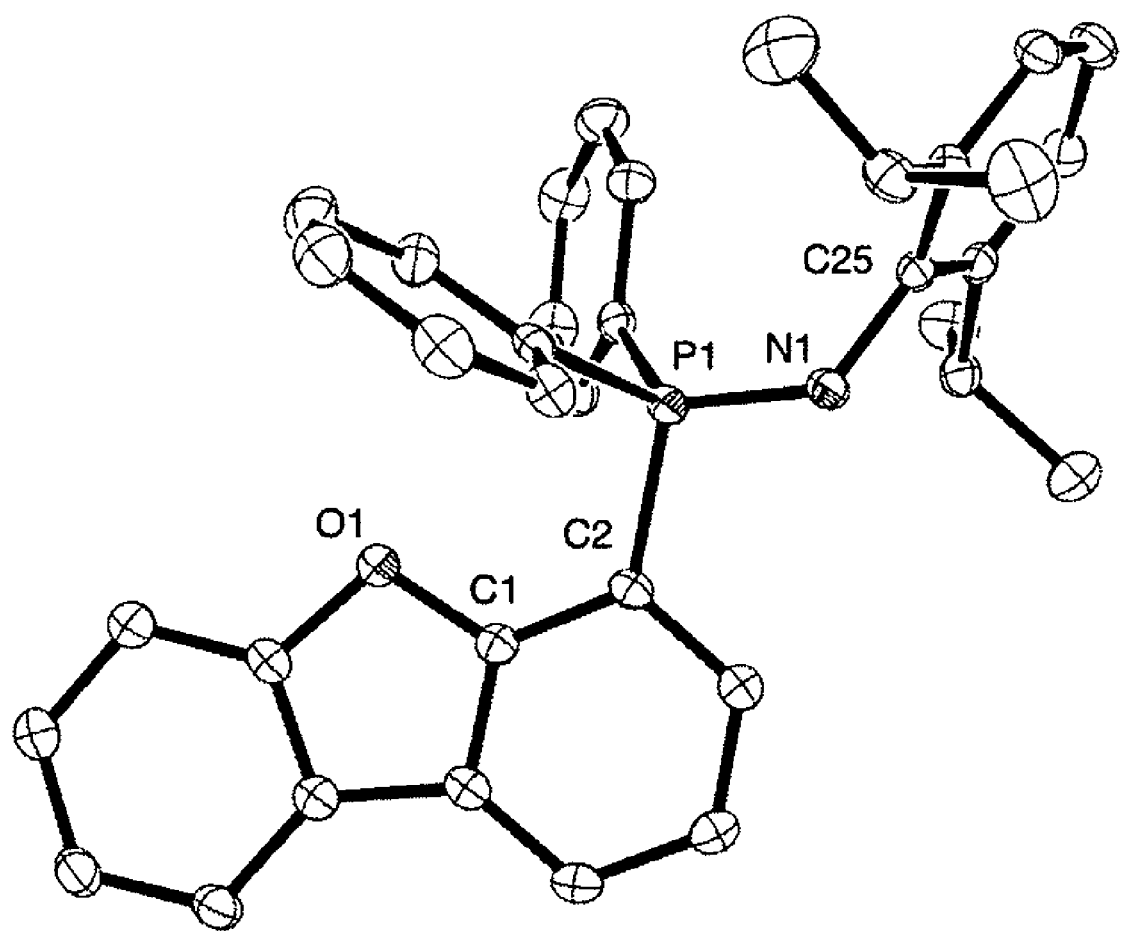
FIG. 1 shows the X-ray crystal structure of a neutral ligand according to one embodiment of the present disclosure.

Unless otherwise indicated, the definitions and embodiments described in this and other sections are intended to be applicable to all embodiments and aspects of the disclosure herein described for which they are suitable as would be understood by a person skilled in the art.

The term "alkyl" as used herein means a straight and/or branched chain, saturated alkyl group and includes methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl and the like.

The term "alkoxy" as used herein means a straight and/or branched chain, saturated alkoxy group and includes methoxy, ethoxy, propoxy, isopropoxy, n-butoxy, s-butoxy, isobutoxy, t-butoxy and the like.

The term "cycloalkyl" as used herein means a monocyclic or polycyclic saturated carbocylic group and includes cyclopropyl, cyclobutyl, cyclopentyl, cyclodecyl, bicyclo[2.2.2]octane, bicyclo[3.1.1]heptane and the like.

The term "aryl" as used herein means a monocyclic or polycyclic aromatic ring system containing from 6 to 14 carbon atoms and at least one aromatic ring and includes phenyl, naphthyl, anthracenyl, 1,2-dihydronaphthyl, 1,2,3,4-tetrahydronaphthyl, fluorenyl, indanyl, indenyl and the like.

The term "fluoro-substituted" with respect to any specified group as used herein means that at least one, including all, of the hydrogen atoms in the group have been replaced with a fluorine.

The term "halo" as used herein means halogen and includes chloro, fluoro, bromo and iodo.

The term "optionally substituted" as used herein means unsubstituted or substituted.

The term "ring system" as used herein refers to a carbon-containing ring system, that includes monocycles, fused bicyclic and polycyclic rings, bridged rings and metallocenes.

The term "polycyclic" as used herein means groups that contain more than one ring linked together and includes, for example, groups that contain two (bicyclic), three (tricyclic) or four (quadracyclic) rings. The rings may be linked through a single bond, a single atom (spirocyclic) or through two atoms (fused and bridged).

The term "coordinating atom" as used herein refers to an atom, for example, phosphorous, nitrogen, oxygen or sulfur, which formally bonds to or shares electrons with the metal center in a chemical bond.

The terms "monodentate", "bidentate" and "tridentate", as used herein relate to the number of coordinating atoms present in a ligand. Accordingly, a monodentate ligand refers to a ligand which bonds to the metal atom through one atom. Bidentate, tridentate and tetradentate ligands contain two, three or four, respectively, atoms that can bind to the metal, although it is not necessary for all of the coordinating atoms to bind to the metal.

The term "non- or weakly-coordinating anion" as used herein refers to an anion which does not formally bond to, or share electrons with, the metal center in a chemical bond. Accordingly, a non- or weakly-coordinating anion does not form strong bonds with the metal center and is easily displaced from the metal centre.

The term "suitable", as in for example, "suitable" reactants, "suitable" groups or "suitable reaction conditions" means that the selection of the particular group, reactant(s) or conditions would depend on the specific synthetic manipulation to be performed and the identity of the molecule but the selection would be well within the skill of a person trained in the art. All process steps described herein are to be conducted under conditions sufficient to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

Catalysts of the Disclosure

The present disclosure includes a catalyst for cyclic lactone polymerization of the formula I:

wherein

L is a neutral ancillary ligand;

M is a divalent metal suitable for cyclic lactone polymerization;

$R^1$ is selected from halo, $R^a$, $OR^a$, $C(O)R^a$, $C(O)OR^a$, $OC(O)R^a$, $C(O)NR^aR^b$ and $NR^aR^b$, wherein $R^a$ and $R^b$ are simultaneously or independently selected from H, $C_{1-10}$alkyl, fluoro-substituted $C_{1-10}$alkyl and $C_{6-14}$aryl, wherein $C_{6-14}$aryl is unsubstituted or substituted with one or more substituents independently selected from halo, $C_{1-6}$alkyl, $NR^aR^b$, $OR^a$ and phenyl; and $X^-$ is a suitable non- or weakly-coordinating anion.

In an embodiment of the disclosure the neutral ancillary ligand comprises at least two coordinating atoms. In a further embodiment, the coordinating atom is nitrogen, oxygen, phosphorous or sulfur.

In another embodiment of the disclosure, the neutral ancillary ligand is a bidentate, tridentate or tetradentate ligand. In a further embodiment, the neutral ancillary ligand is a bidentate ligand. In another embodiment, the neutral ancillary ligand is a bidentate ligand and the coordinating atoms are oxygen and/or nitrogen.

In a further embodiment, the neutral ancillary ligand comprises at least one atom which can be protonated.

In an embodiment of the disclosure, the neutral ligand is chiral.

In a further embodiment, the neutral ligand is a monocyclic, bicyclic or tricyclic ligand.

In another embodiment of the disclosure, the neutral ancillary ligand is a compound of the formula (V)

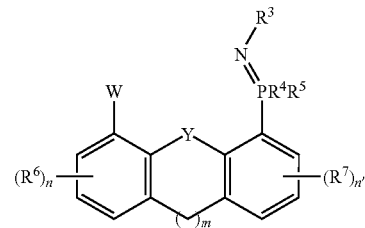

wherein

Y is O or S;

$R^3$ is selected from $C_{1-20}$alkyl, $C_{3-20}$cycloalkyl, $C_{6-14}$aryl and $Si(R^c)_3$, said latter 4 groups being optionally substituted with one or more substituents independently selected from $C_{1-6}$alkyl, fluoro-substituted $C_{1-6}$alkyl, phenyl, phenyl substituted with one to five $C_{1-6}$alkyl, and halo, wherein $R^c$ is selected from $C_{1-20}$alkyl, fluoro-substituted $C_{1-20}$alkyl, $C_{3-20}$cycloalkyl and $C_{6-14}$aryl;

$R^4$ and $R^5$ are simultaneously or independently selected from $C_{1-20}$alkyl, $C_{3-20}$cycloalkyl and $C_{6-14}$aryl, said latter 3 groups being optionally substituted with one or more substituents independently selected from $C_{1-6}$alkyl, fluoro-substituted $C_{1-6}$alkyl and halo;

$R^6$ and $R^7$ are simultaneously or independently selected from $C_{1-6}$alkyl, fluoro-substituted $C_{1-6}$alkyl and halo;

W is a H, a chiral group or $-P(R^6R^9)=N-R^{19}$, wherein $R^8$, $R^9$ and $R^{10}$ are as defined for $R^4$, $R^5$ and $R^3$, respectively;

m is 0, 1 or 2; and n and n' are simultaneously or independently 0, 1, 2 or 3.

In an embodiment of the disclosure Y is O.

In an embodiment of the disclosure, $R^3$ is selected from $C_{1-10}$alkyl, $C_{3-10}$cycloalkyl, phenyl, naphthyl, and $Si(R^c)_3$, said latter 5 groups being optionally substituted, wherein $R^c$ is selected from $C_{1-10}$alkyl, fluoro-substituted $C_{1-10}$alkyl, $C_{3-10}$cycloalkyl, phenyl and naphthyl. In a further embodiment, $R^3$ is selected from $C_{1-6}$alkyl, $C_{3-6}$cycloalkyl, phenyl and $Si(R^c)_3$, said latter 4 groups being optionally substituted, wherein $R^c$ is selected from $C_{1-6}$alkyl, fluoro-substituted $C_{1-6}$alkyl, $C_{3-6}$cycloalkyl and phenyl. In another embodiment, $R^3$ is selected from optionally substituted phenyl. It is an embodiment that the substituents on $R^3$ are selected from one to five, suitably one to three, of $C_{1-4}$alkyl, fluoro-substituted $C_{1-4}$alkyl, phenyl, phenyl substituted with one to three $C_{1-4}$alkyl, and halo, suitably $C_{1-4}$alkyl. In a further embodiment, $R^3$ is

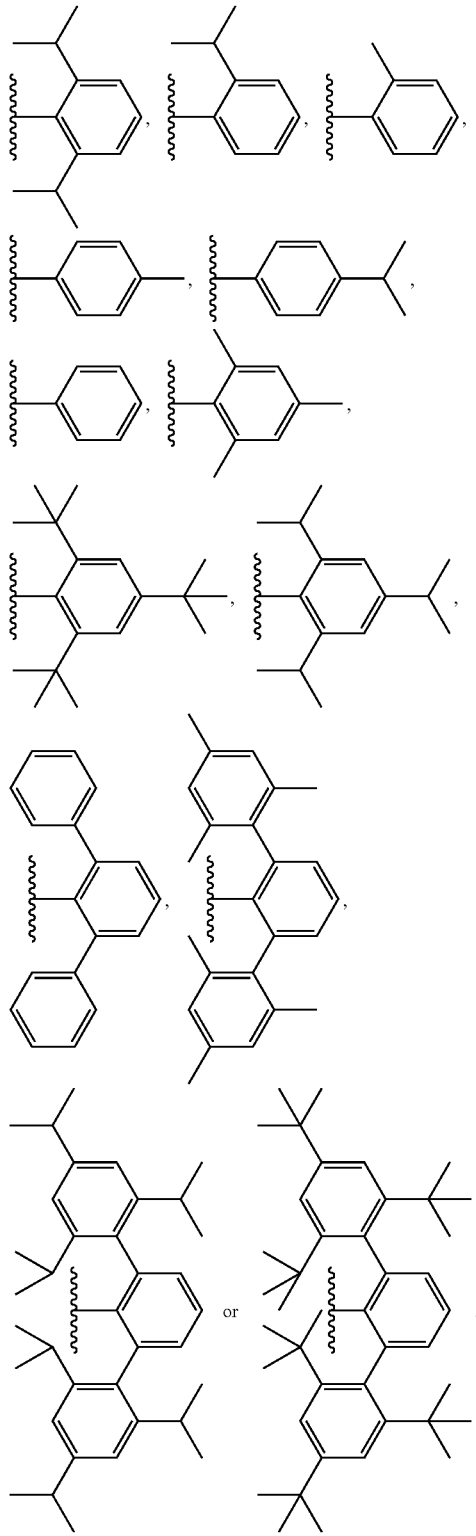

In embodiments of the disclosure, $R^4$ and $R^5$ are simultaneously or independently selected from $C_{1-10}$alkyl, $C_{3-10}$cycloalkyl, naphthyl and phenyl, said latter 4 groups being optionally substituted. In a further embodiment $R^4$ and $R^5$ are simultaneously or independently selected from $C_{1-6}$alkyl, $C_{3-6}$cycloalkyl and phenyl, said latter 3 groups being optionally substituted. In a further embodiment $R^4$ and $R^5$ are simultaneously selected from $C_{1-6}$alkyl and phenyl, said latter 2 groups being optionally substituted. In an embodiment of the disclosure the optional substituents on $R^4$ and $R^5$ are independently selected from one to five, suitably one to three, of $C_{1-4}$alkyl, fluoro-substituted $C_{1-4}$alkyl and halo. In an embodiment $R^4$ and $R^5$ are both unsubstituted phenyl.

In an embodiment of the disclosure, $R^6$ and $R^7$ are simultaneously or independently selected from $C_{1-4}$alkyl, fluoro-substituted $C_{1-6}$alkyl and halo, suitably $CH_3$, $CF_3$, F, Cl or Br.

In an embodiment of the disclosure W is H.

In another embodiment of the disclosure, W is —P($R^8R^9$)=N—$R^{10}$.

In a further embodiment of the disclosure, $R^{10}$ is selected from $C_{1-10}$alkyl, $C_{3-10}$cycloalkyl, phenyl, naphthyl and Si($R^d$)$_3$, said latter 5 groups being optionally substituted, wherein $R^d$ is selected from $C_{1-10}$alkyl, fluoro-substituted $C_{1-10}$alkyl, $C_{3-10}$cycloalkyl, phenyl and naphthyl. In a further embodiment, $R^{10}$ is selected from $C_{1-6}$alkyl, $C_{3-6}$cycloalkyl, phenyl and Si($R^d$)$_3$, said latter 4 groups being optionally substituted, wherein $R^d$ is selected from $C_{1-6}$alkyl, fluoro-substituted $C_{1-6}$alkyl, $C_{3-6}$cycloalkyl, and phenyl. In another embodiment, $R^{10}$ is selected from optionally substituted phenyl. It is an embodiment that the substituents on $R^{10}$ are selected from one to five, suitably one to three, of $C_{1-4}$alkyl, fluoro-substituted $C_{1-4}$alkyl, phenyl, phenyl substituted with one to three $C_{1-4}$alkyl, and halo, suitably $C_{1-4}$alkyl. In a further embodiment, $R^{10}$ is

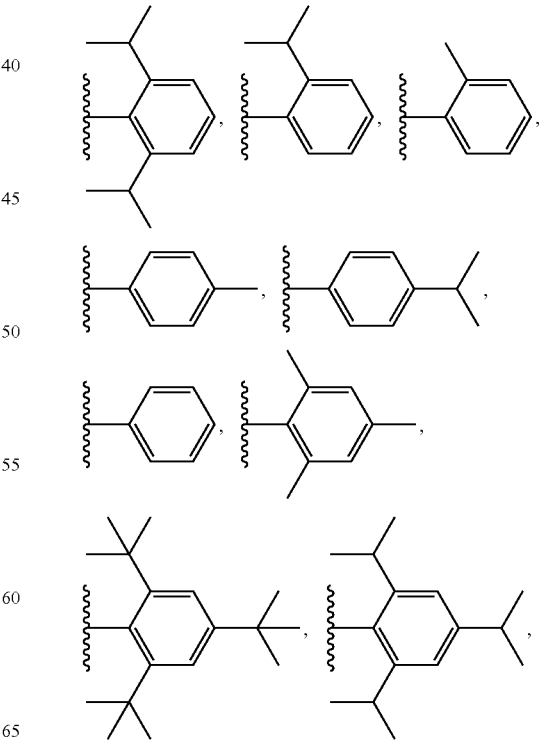

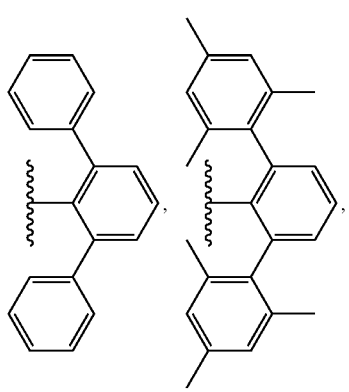

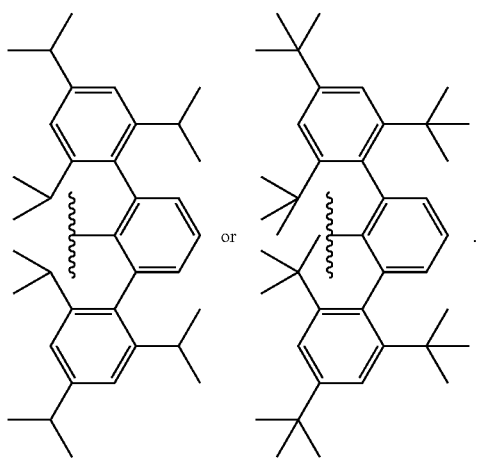

In another embodiment of the disclosure, $R^8$ and $R^9$ are simultaneously or independently selected from $C_{1-10}$alkyl, $C_{3-10}$cycloalkyl, naphthyl and phenyl, said latter 4 groups being optionally substituted. In a further embodiment $R^8$ and $R^9$ are simultaneously or independently selected from $C_{1-6}$alkyl, $C_{3-6}$cycloalkyl and phenyl, said latter 3 groups being optionally substituted. In a further embodiment $R^8$ and $R^9$ are simultaneously selected from $C_{1-6}$alkyl and phenyl, said latter 2 groups being optionally substituted. In an embodiment of the disclosure the optional substituents on $R^8$ and $R^9$ are independently selected from one to five, suitably one to three, of $C_{1-4}$alkyl, fluoro-substituted $C_{1-4}$alkyl and halo. In an embodiment $R^8$ and $R^9$ are both unsubstituted phenyl.

In another embodiment of the disclosure, W is any suitable chiral group which is able to control the stereochemistry of the resultant polymer during the catalytic polymerization of a cyclic ester. It will be understood by those skilled in the art that the chiral group W is able to control the stereochemistry of the resultant polylactide as a result of the chiral group being proximal to the reactive metal center. Accordingly, the chiral group W is able to stereochemically control the entry of the substrate into the reaction center, resulting in the production of a polymer possessing desired properties. Examples of suitable chiral groups which are able to control the stereochemistry during the catalytic polymerization include menthol, binaphthyl, camphor, and phosphorous containing moieties such as, but not limited to,

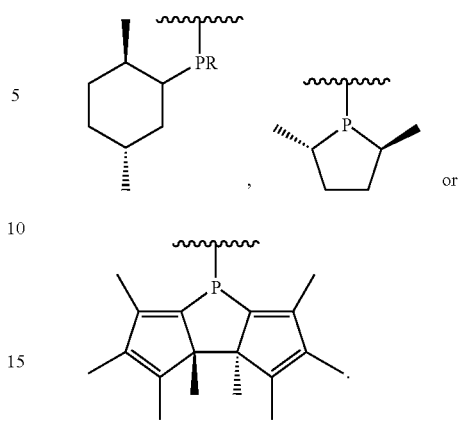

In an embodiment of the disclosure m, n and n' are all 0.

In a further embodiment of the disclosure, the neutral ancillary ligand is compound 2, 6a, 6b, 6c, 6d or 6e having the formulae as shown in the Examples herein below.

In an embodiment of the disclosure M is $Ca^{2+}$, $Mg^{2+}$ or $Zn^{2+}$. In an embodiment of the disclosure, $R^1$ is selected from Cl, $C_{1-10}$alkyl, $C_{1-10}$alkoxide, phenyl and $NR^aR^b$, said latter 4 groups being optionally substituted with one or more substituents independently selected from $C_{1-4}$alkyl, fluoro-substituted $C_{1-4}$alkyl and F, wherein $R^a$ and $R^b$ are simultaneously or independently selected from H, $C_{1-10}$alkyl, fluoro-substituted $C_{1-10}$alkyl and phenyl, where $R^a$ and $R^b$ are not simultaneously H.

In another embodiment of the disclosure $X^-$ is selected from $[B(C_6F_5)_4]^-$, $[B(C_6H_5)_4]^-$, $[B(3,5-(CF_3)_2C_6H_3)_4]^-$ and $[SO_3CF_3]^-$.

In another embodiment of the disclosure, the catalyst of formula I is (4a)

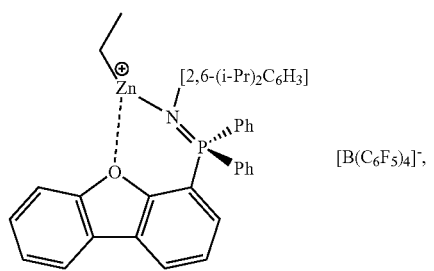

(4b)

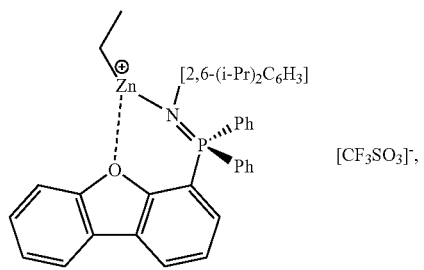

(9a) 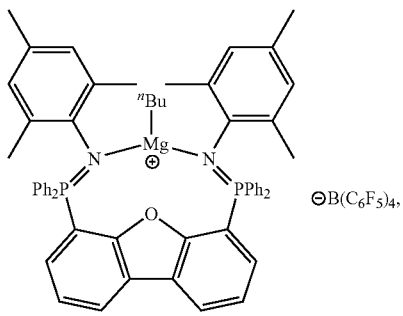 ⊖B(C₆F₅)₄, (9b) 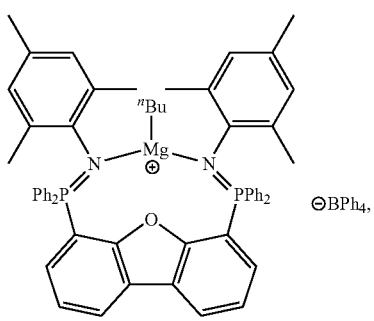 ⊖BPh₄, (9c) 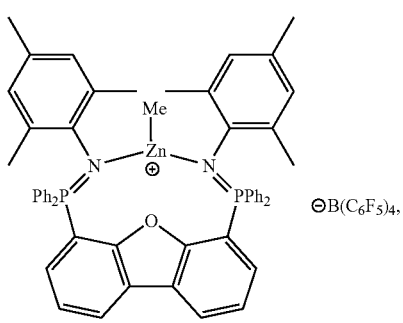 ⊖B(C₆F₅)₄, (9d) 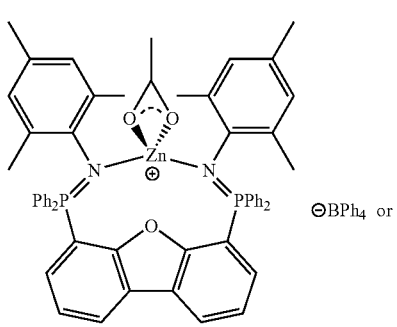 ⊖BPh₄ or (9e) 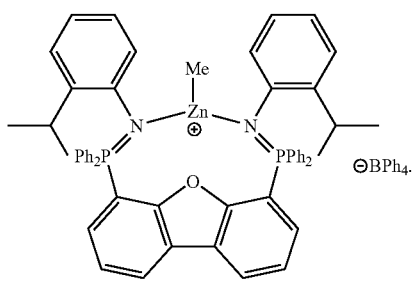 ⊖BPh₄.

Methods/Processes of the Disclosure

The present disclosure also includes methods of preparing the catalysts of formula I. Accordingly, in one embodiment, the catalysts of formula I are prepared by reacting a compound of formula II:

$$LMR^1R^2 \quad (II)$$

wherein

L is a neutral ancillary ligand;

M is a divalent metal suitable for cyclic lactone polymerization; and $R^1$ and $R^2$ are independently selected from $R^1$ is selected from halo, $R^a$, $OR^a$, $C(O)R^a$, $C(O)OR^a$, $OC(O)R^a$, $C(O)NR^aR^b$ and $NR^aR^b$, wherein $R^a$ and $R^b$ are simultaneously or independently selected from H, fluoro-substituted $C_{1-10}$alkyl and $C_{6-14}$aryl wherein $C_{6-14}$aryl is unsubstituted or substituted with one or more substituents independently selected from halo, $C_{1-6}$alkyl, $NR^aR^b$, $OR^a$ and phenyl, with a suitable Brønsted acid or Lewis Acid under conditions for the formation of the compound of formula I.

In an embodiment of the disclosure, the Brønsted acid is any suitable acid that is able to protonate the compound of formula II, yet which provides a counter anion that will not coordinate strongly to the divalent metal M. Examples of such acids are well known in the art and include, but are not limited to an anilinium acid or a sulfonic acid, such as [HNMe₂Ph][B(C₆F₅)₄] or triflic acid.

In an embodiment of the disclosure, the Lewis Acid is any suitable Lewis acid that is able to abstract one of the $R^1$ or $R^2$ groups, to form a counter anion that will not coordinate strongly to the divalent metal M. Examples of such acids are well known in the art and include, but are not limited to, B(C₆F₅)₃ or BPh₃.

In embodiments of the disclosure, the conditions suitable for the formation of a compound of formula I include using a slight excess of the Brønsted acid or Lewis Acid over the compound of formula II, suitably about 1.5 equivalents of the Brønsted acid or Lewis Acid, more suitably about 1.2 equivalents, most suitably about 1.1 equivalents. In further embodiments, the suitable conditions also include performing the reaction in an organic solvent, such as benzene, toluene, bromobenzene, xylenes, DMF, acetonitrile and the like. In embodiments of the disclosure, the reaction is performed at about room temperature, suitably about 22° C.

In a further embodiment, the present disclosure includes a process for the preparation of a catalyst of formula I comprising:

(a) reacting a neutral ancillary ligand (L) with a suitable Brønsted acid under conditions to form a protonated ligand of the formula III:

$$[LH]^+X^- \quad (III)$$

wherein L is a neutral ancillary ligand; and

X is a suitable non- or weakly-coordinating anion; and (b) reacting the compound of formula III with a compound of the formula IV:

$$MR^1R^2 \quad (IV)$$

wherein M is a divalent metal suitable for cyclic lactone polymerization; and $R^1$ and $R^2$ are independently selected from $R^1$ is selected from halo, $R^a$, $OR^a$, $C(O)R^a$, $C(O)OR^a$, $OC(O)R^a$, $C(O)NR^aR^b$ and $NR^aR^b$, wherein $R^a$ and $R^b$ are simultaneously or independently selected from H, $C_{1-10}$alkyl, fluoro-substituted $C_{1-10}$alkyl and $C_{6-14}$aryl, wherein $C_{6-14}$aryl is unsubstituted or substituted with one or more substituents independently selected from halo, $C_{1-6}$alkyl, $NR^aR^b$, $OR^a$ and phenyl, under conditions for the formation of the compound of formula I.

In embodiments of the disclosure, the conditions suitable for the formation of a compound of formula III include using a slight excess of the Brønsted acid over the neutral ancillary ligand (L), suitably about 1.5 equivalents of the Brønsted acid, more suitably about 1.2 equivalents, most suitably about 1.1 equivalents. In further embodiments, the suitable conditions also include performing the reaction in an organic solvent, such as benzene, toluene, bromobenzene, xylenes, DMF, acetonitrile and the like. In embodiments of the disclosure, the reaction is performed at about room temperature, suitably about 22° C.

In further embodiments of the disclosure, the conditions suitable for the formation of a compound of formula I include using a slight excess of the compound of the formula IV over the compound of formula III, suitably about suitably about 1.5 equivalents of the compound of the formula IV, more suitably about 1.2 equivalents, most suitably about 1.1 equivalents. In further embodiments, the suitable conditions also include performing the reaction in an organic solvent, such as hexane, tetrahydrofuran, bromobenzene, acetonitrile, toluene, benzene, xylenes, pyridine, DMF and the like. In embodiments of the disclosure, the reaction is performed at an increased temperature, suitably about 50° C. to about 150° C., more suitably about 75° C. to about 125° C., most suitably about 100° C.

Again, the Brønsted acid is any suitable acid that is able to protonate the compound of formula II or formula V, yet which provides a counter anion that will not coordinate strongly to the divalent metal M. Examples of such acids are well known in the art and include, but are not limited to an anilinium acid or a sulfonic acid, such as [HNMe$_2$Ph][B(C$_6$F$_5$)$_4$], NaBPh$_4$/HCl or triflic acid.

In an embodiment of the disclosure, the protonated ligand [LH]$^+$X$^-$ (formula III) is a stable solid in air. In another embodiment of the disclosure, the protonated ligand [LH]$^+$X$^-$ (formula III) is a not a stable solid in air.

In the above described methods, the definitions for L, M, R$^1$, R$^2$ and X, and the embodiments thereof, are the same as those described above for the catalysts of formula I.

Compounds of formula (IV) are well known in the art and are either commercially available or are prepared using methods known in the art.

The neutral ligands of the formula V are either commercially available or are prepared by reaction of the corresponding phosphine precursor according to a modified literature procedure, with an appropriate aryl-azide under Staudinger conditions.[5,6] In an embodiment of the disclosure, as seen in Scheme 1, a compound of the formula (V), wherein R$^1$, R$^2$, R$^3$, R$^6$, R$^7$, Y and m are as defined in formula V and W is H or —P(R$^8$R$^9$)=N—R$^{10}$, wherein R$^8$, R$^9$ and R$^{10}$ are as defined in formula V, is prepared by reaction of a corresponding phosphine of formula VI, wherein R$^1$, R$^2$, R$^3$, R$^6$, R$^7$, Y and m are as defined in formula V and R$^e$ is H or PR$^8$R$^9$, wherein R$^8$ and R$^9$ are as defined in formula V, with one (R$^e$=H) or two (R$^e$=PR$^8$R$^9$) equivalents of an aryl azide of the formula R$^3$—N$_3$, wherein R$^3$ is as defined in formula V.

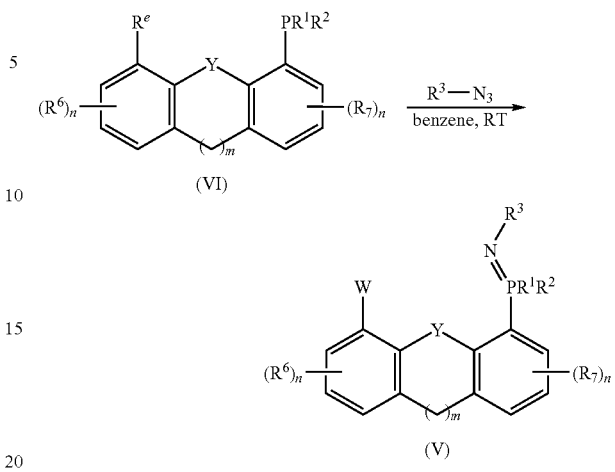

Scheme 1

Compounds of formula VI are either commercially available or are prepared from the corresponding dibenzofuran or dibenzopyran using known reaction conditions (for example as described in Kranenburg et al.[7]).

In an embodiment of the present application, installation of a group other than —P(R$^8$R$^9$)=N—R$^{10}$ as W is achieved by reacting a compound of the formula VI, wherein R$^1$, R$^2$, R$^3$, R$^6$, R$^7$, Y and m are as defined in formula V and R$^e$ is H under conditions to form the corresponding lithio compound (i.e. wherein R$^e$ is Li) followed by reaction with the appropriate electrophilic reagent, e.g. a halo containing precursor to the desired group. Such methods would be known to a person skilled in the art.

In an embodiment, the cationic divalent metal catalysts of the formula I are useful for the polymerization of cyclic lactones. Accordingly, the present disclosure also includes a method for the polymerization of one or more cyclic lactones comprising contacting the one or more cyclic lactones with a divalent metal catalyst of the formula I as described herein under conditions for the polymerization of the cyclic lactone. In an embodiment, the cyclic lactone is lactide, glycolide, ε-caprolactone, dioxanone, 1,4-dioxane-2,3-dione, beta-propiolactone, tetramethyl glycolide, beta-butyrolactone, gammabutyrolactone or pivalolactone, or cyclic carbonates such as trimethylene carbonate, 2,2-dimethyl trimethylene carbonate and the like. In a further embodiment, the cyclic lactone is lactide or ε-caprolactone, suitably lactide.

In an embodiment of the disclosure, the conditions for the polymerization of the cyclic lactone comprise the use of a catalyst of the formula I in an amount of about 0.01 mol % to about 20 mol %, suitably about 0.1 mol % to about 10 mol %, more suitably about 1 mol %. In another embodiment, the conditions for the polymerization of the cyclic lactone also comprise a temperature of about −25° C. to about 150° C. In another embodiment, the polymerization reaction is carried out at a temperature of about 25° C. to about 100° C. In a further embodiment, the polymerization reaction is carried out at about 50° C. In another embodiment, the polymerization reaction is carried out at about room temperature, suitably at about 22° C. In further embodiments, the conditions for the polymerization of the cyclic lactone also include performing the reaction in an organic solvent, such as hexanes, tetrahydrofuran, toluene, benzene, bromobenzene, acetonitrile, xylenes, pyridine, DMF and the like.

The following non-limiting examples are illustrative of the present disclosure:

EXAMPLES

Example 1

Synthesis of 4-(PPh$_2$)dibenzofuran (1)

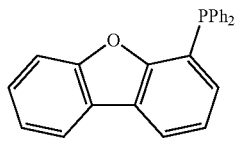

(1)

Compound (1) has been prepared according to a modified literature procedure.[5] A 2-neck 100 mL round-bottom flask attached to a swivel frit apparatus was charged with dibenzofuran (1.03 g 6.12 mmol) and 35 mL of Et$_2$O. The vessel was cooled to −78° C. and 1.7M $^t$BuLi in pentane (4.0 mL, 6.8 mmol) was subsequently added dropwise. A white precipitate was noted within minutes. The suspension was allowed to stir for 1.5 hours at −78° C. and then warmed slowly to room temperature with stirring over an additional 1 hour. The system was cooled to −78° C. and neat ClPPh$_2$ (6.5 mL, 37 mmol) was added over 5 minutes. The reaction mixture was allowed to gradually warm to room temperature over 12 hours yielding a white suspension. Et$_2$O was removed under vacuum and approximately 50 mL of pentane was added by vacuum transfer. The resulting white suspension was sonicated for 5 minutes and filtered, yielding a white solid mixture of (PPh$_2$C$_4$H$_3$)$_2$C$_4$O and LiCl in 71% yield (1.78 g, 4.35 mmol). The spectral data matched the published results.

Example 2

Synthesis of the Ligand 4-(DippNPPh$_2$)C$_{12}$H$_7$O (2)

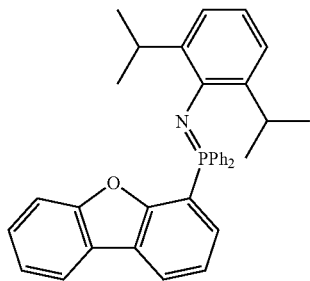

(2)

A 2-neck 100 mL round-bottom flask attached to a swivel frit apparatus was charged with a mixture of (1) (1.22 g, 3.45 mmol) and residual LiCl. Approximately 35 mL of toluene was transferred to the reaction vessel. Excess (2,6-di-isopropyl)-phenyl-azide (DippN$_3$) (0.463 g, 2.28 mmol) was added and the reaction mixture was allowed to stir under Ar at room temperature. Within minutes of initiating the reaction, evolution of N$_2$ was observed and the solution turned light yellow. The reaction mixture was stirred for 12 hours at room temperature producing a cloudy yellow solution. Filtration to remove residual LiCl yielded a clear yellow solution, which gave a crude yellow oily substance upon removal of toluene in vacuo. Approximately 60 mL of pentane was added by vacuum transfer to the crude product, and the mixture was vigorously stirred for two hours. Filtration of the resulting suspension yielded the product as a white powder which was washed three times with 10 mL portions of pentane and dried under vacuum, affording the desired product in 79% yield (0.922 g, 1.75 mmol). $^1$H NMR (C$_6$D$_6$): δ 7.89-7.80 (ov m, 5H, ortho-Ph+Aromatic H), 7.61 (d, 1H, J=6.0 Hz, Aromatic H), 7.51 (m, 1H, Aromatic H), 7.14 (ov m, 2H, meta-Dipp), 7.04-6.93 (br ov m, 11 H, Aromatic H), 3.68 (sp, 2H, J$_{HH}$=6.9 Hz, CH(CH$_3$)$_2$), 1.06 (d, 12H, J$_{HH}$=6.9 Hz, CH(CH$_3$)$_2$). $^{31}$P{$^1$H} NMR (C$_6$D$_6$): δ −13.4 (s). $^{13}$C{$^1$H} NMR (C$_6$D$_6$): δ 157.36, 156.89, 145.06, 143.24 (d, J$_{PC}$=6.8 Hz), 134.66, 133.23, 132.90 (d, J$_{PC}$=10.6 Hz), 132.23 (d, J$_{PC}$=5.3 Hz), 131.61 (d, J$_{PC}$=3.0 Hz), 128.84 (d, J$_{PC}$=12.8 Hz), 128.69, 124.59 (d, J$_{PC}$=2.3 Hz), 123.73, 123.55, 123.45 (d, J$_{PC}$=1.5 Hz), 123.32, 121.08, 120.45 (d, J$_{PC}$=3.0 Hz), 118.70, 112.42, 29.40 (CH(CH$_3$)$_2$), 24.37 (CH(CH$_3$)$_2$). Anal. Calcd. (%) for C$_{36}$H$_{34}$NOP: C, 81.95; H, 6.50; N, 2.65. found: C, 81.54; H, 6.75; N, 2.56.

Example 3a

Synthesis of Cationic Ligand (2)$^+$[B(C$_6$F$_5$)$_4$]$^-$ (3a)

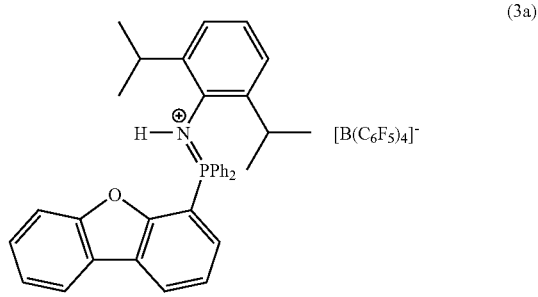

(3a)

Under an argon atmosphere, neutral ligand (2) (0.098 g, 0.186 mmol) was combined with an equivalent of the anilinium activator [HNMe$_2$Ph][B(C$_6$F$_5$)$_4$] (0.150 g, 0.187 mmol) in 2 mL of benzene. Immediately upon combining the reagents, the formation of a pale yellow oil was observed. The reaction mixture was allowed to stir for 5 minutes at room temperature, and then the benzene was decanted. The remaining oil was washed twice with pentane and dried under vacuum to generate protonated ligand (3a) as a white powder in 97% yield (0.217 g, 0.180 mmol). $^1$H NMR (3:1 C$_6$D$_6$/C$_6$D$_5$Br): δ 7.84 (d, 1H, 7.8 Hz, Aromatic H), 7.61 (m, 1H, Aromatic H), 7.14-7.05 (ov m, 8H, Aromatic H) 6.96 (ov m, 5H, meta-Ph+Aromatic H), 6.90 (d, 1H, J=6.9 Hz, Aromatic H), 6.86-6.72 (ov m, 2H, Aromatic H), 6.68 (d, 2H, J=7.8 Hz, meta-Dipp), 4.96 (d, 1H, $^2$J$_{HP}$=9.3 Hz, NH), 2.66 (sp, 2H, J=6.9 Hz, CH(CH$_3$)$_2$), 0.56 (d, 12H, J=6.9 Hz, CH(CH$_3$)$_2$). $^{31}$P{$^1$H} NMR (1:1 C$_6$D$_6$/C$_6$D$_5$Br): δ 36.10. $^{13}$C{$^1$H} NMR (1:1 C$_6$D$_6$/C$_6$D$_5$Br): δ 156.80, 156.09, 150.37 (br, C$_6$F$_5$), 147.56 (d, J$_{PC}$=3.0 Hz), 147.22 (br, C$_6$F$_5$), 138.33 (br, C$_6$F$_5$), 136.00 (d, J$_{PC}$=2.3 Hz), 135.10 (br, C$_6$F$_5$), 133.40 (d, J$_{PC}$=11.3 Hz), 130.02 (d, J$_{PC}$=14 Hz), 128.77 (d, J$_{PC}$=3.0 Hz), 128.37, 126.45 (d, J$_{PC}$=6.9 Hz), 124.86, 124.54, 124.10 (d, J$_{PC}$=12 Hz), 122.75, 121.91, 121.57, 118.45, 117.01, 111.45, 106.30, 104.98, 28.97 (CH(CH$_3$)$_2$), 22.83 (CH(CH$_3$)$_2$). $^{19}$F NMR (1:1 C$_6$D$_6$/C$_6$D$_5$Br): δ −131.67 (d, 8F, ortho-C$_6$F$_5$), −162.42 (t, 4F, para-C$_6$F$_5$), −166.26 (t, 8F, meta- $C_6F_5$). Anal. Calcd. (%) for $C_{60}H_{35}BF_{20}NOP$: C, 59.67; H, 2.92; N, 1.16. found: C, 59.97; H, 3.37; N, 1.37.

Example 3b

Synthesis of Cationic Ligand $(2)^+[SO_3CF_3]^-$ (3b)

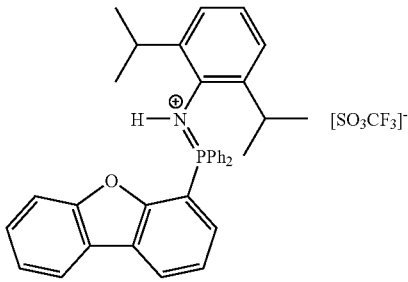

(3b)

To a solution of ligand (2) (1.00 g, 1.90 mmol) in 30 mL of benzene under an argon atmosphere a slight excess of triflic acid (0.170 mL, 1.92 mmol) was added. Upon addition of triflic acid, a color change of the solution from yellow to pale yellow was observed. The solution was allowed to stir for 30 minutes at room temperature, at which time the benzene was removed under vacuum. The crude product was then stirred in 30 mL of pentane for 30 minutes and filtered. The crude residue was washed with pentane (3×10 mL) and dried under vacuum to yield (3b) as an analytically pure white powder in 85% yield (1.10 g, 1.62 mmol). $^1$H NMR (1:1 $C_6D_6/C_6D_5Br$): δ 9.31 (d, 1H, $^2J_{PH}$=11.7 Hz, NH), 7.73 (ov m, 5H, ortho-Ph+ Aromatic H), 7.61 (dd, 1H, J=14 Hz, 8.1 Hz, Aromatic H), 7.53 (d, 1H, J=6.6 Hz, Aromatic H), 7.20-7.00 (ov m, 9H, Aromatic H), 6.92-6.80 (ov m, 2H, Aromatic H), 6.73 (d, 2H, $^2J_{HP}$=7.5 Hz, meta-Dipp), 3.23 (sp, 2H, J=6.9 Hz, CH(CH$_3$)$_2$), 0.85 (br s, 12H, CH(CH$_3$)$_2$). $^{31}$P{$^1$H} NMR (1:1 $C_6D_6/C_6D_5Br$): δ 33.5. $^{13}$C{$^1$H} NMR (1:1 $C_6D_6/C_6D_5Br$): δ 157.45, 156.97, 149.25 (d, J=3.8 Hz), 135.35, 134.58 (d, $J_{PC}$=11.3 Hz), 133.15 (d, $J_{PC}$=7.6 Hz), 130.95 (d, $J_{PC}$=6.7 Hz), 130.13, 129.45 (d, $J_{PC}$=4.5 Hz), 129.16, 124.74, 124.57, 123.53, 122.64, 122.64, 121.75, 121.60, 112.94, 105.90, 104.50, 30.06 (CH(CH$_3$)$_2$), 24.20 (CH(CH$_3$)$_2$). $^{19}$F NMR (1:1 $C_6D_6/C_6D_5Br$): δ −77.49. Anal. Calcd. (%) for $C_{37}H_{35}F_3NO_4PS$: C, 65.57; H, 5.21; N, 2.07; S, 4.73. found: C, 66.09; H, 5.33; N, 2.14; S, 4.93.

Example 4a

Synthesis of Catalyst $[(3a)ZnEt]^+$ (4a)

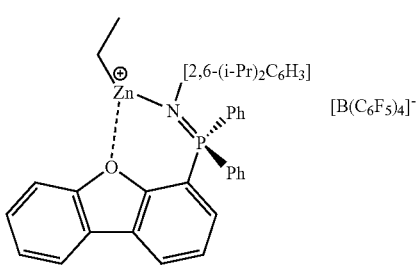

(4a)

Under an argon atmosphere, a slight excess of diethylzinc (21 μL, 0.127 mmol) was added to a solution of (3a) (150 mg, 0.124 mmol) in 5 mL of toluene. The reaction mixture was heated to 100° C. for 16 hours, and the solvent was then removed under vacuum. The crude product was dissolved in a minimum amount of bromobenzene and precipitated as a pale yellow oil by addition of pentane. The solvent was decanted, the oil was washed twice with pentane, and dried under vacuum to yield (4a) as a white powder in 87% yield (141 mg, 0.108 mmol). $^1$H NMR (1:1 $C_6D_6/C_6D_5Br$): δ 7.85 (d, J=7.5 Hz, 1H, Aromatic H), 7.66 (dd, 1H, J=4.8 Hz, 3.0 Hz, Aromatic H), 7.25-6.96 (ov m, 15H, Aromatic H), 6.83-6.73 (ov m, 3H, meta-Dipp+Aromatic H), 2.72 (sp, 2H, J=6.9 Hz, CH(CH$_3$)$_2$), 1.00 (t, 3H, J=7.8 Hz, CH$_2$CH$_3$), 0.81 (d, 6H, J=6.9 Hz, CH(CH$_3$)$_2$), 0.73 (q, 2H, J=7.8 Hz, CH$_2$CH$_3$), 0.31 (d, 6H, J=6.9 Hz, CH(CH$_3$)$_2$). $^{31}$P{$^1$H} NMR (1:1 $C_6D_6/C_6D_5Br$): δ 30.1. $^{13}$C{$^1$H} NMR (1:1 $C_6D_6/C_6D_5Br$): δ 157.11, 156.38, 150.96 (br, $C_6F_5$), 147.76 (br, $C_6F_5$), 146.88 (d, $J_{PC}$=4.5 Hz), 138.88 (br, $C_6F_5$), 136.36 (d, $J_{PC}$=3.0 Hz), 135.61 (br, $C_6F_5$), 133.40 (d, $J_{PC}$=9.8 Hz), 132.68 (d, $J_{PC}$=8.3 Hz), 131.03 (d, $J_{PC}$=13 Hz), 130.37, 129.91, 129.11, 126.90 (d, $J_{PC}$=6.8 Hz), 126.28, 125.58, 125.47, 122.62, 122.50 (d, $J_{PC}$=0.8 Hz), 112.32, 111.68, 111.03, 100.79, 29.68 (CH (CH$_3$)$_2$), 25.82 (CH(CH$_3$)$_2$), 21.68 (CH(CH$_3$)$_2$), 11.03 (CH$_2$CH$_3$), 4.65 (CH$_2$CH$_3$). $^{19}$F NMR (1:1 $C_6D_6/C_6D_5Br$): δ −131.63 (d, 8F, ortho-$C_6F_5$), −162.36 (t, 4F, para-$C_6F_5$), −166.15 (t, 8F, meta-$C_6F_5$). Anal. Calcd. (%) for $C_{62}H_{39}BF_{20}NOPZn$: C, 57.23; H, 3.02; N, 1.08. found: C, 57.08; H, 3.10; N, 1.21.

Example 4b

Synthesis of Catalyst $[(3b)ZnEt]^+$ (4b)

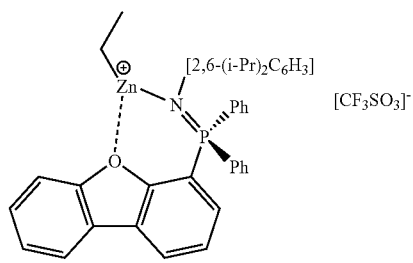

(4b)

Under an argon atmosphere, a slight excess of diethylzinc (80 μL, 0.486 mmol) was added to a solution of (3b) (303 mg, 0.447 mmol) in benzene (50 mL). The reaction mixture was then allowed to stir at 100° C. for 24 hours. The benzene solvent was removed under vacuum, yielding the crude product as an off-white solid. The residue was dissolved in a minimum amount of bromobenzene and precipitated as a white powder by addition of pentane. The solvent was decanted, and the product was washed again with a small portion of pentane. Drying under vacuum gave (4b) as a white powder in 83% yield (288 mg, 373 mmol). $^1$H NMR (1:1 $C_6D_6/C_6D_5Br$): δ 7.70 (ov m, 2H, Aromatic H), 7.58 (d, 1H, J=6.6 Hz, Aromatic H), 7.44 (broad, 4H, ortho-Ph), 7.15-6.70 (ov m, 13H, Aromatic H), 3.51 (sp, 2H, J=6.9 Hz, CH(CH$_3$)$_2$), 1.36 (t, 3H, J=8.1 Hz, CH$_2$CH$_3$), 1.32 (d, 6H, J=6.9 Hz, CH(CH$_3$)$_2$), 0.80 (q, 2H, J=8.1 Hz, CH$_2$CH$_3$), 0.32 (d, 6H, J=6.9 Hz, CH(CH$_3$)$_2$). $^{31}$P{$^1$H} NMR (1:1 $C_6D_6/C_6D_5Br$): δ

26.93. $^{13}C\{^1H\}$ NMR (1:1 $C_6D_6/C_6D_5Br$): δ 158.78, 156.97, 147.14 (d, $J_{PC}$=5.3 Hz), 139.07 (d, $J_{PC}$=8.3 Hz), 134.60 (d, $J_{PC}$=9.8 Hz), 133.16, 133.85 (d, $J_{PC}$=3.0 Hz), 129.83, 129.61 (d, $J_{PC}$=12.1 Hz), 129.15, 127.73 (d, $J_{PC}$=6.8 Hz), 126.86 (d, $J_{PC}$=3.8 Hz), 125.27, 125.15 (d, $J_{PC}$=3.0 Hz), 124.53 (d, $J_{PC}$=12.8 Hz), 123.38, 121.94, 112.98, 110.77, 109.27, 29.73 (CH(CH$_3$)$_2$), 25.86 (CH(CH$_3$)$_2$), 23.05 (CH(CH$_3$)$_2$), 12.61 (CH$_2$CH$_3$), 2.34 (d, $^3J_{PC}$=2.7 Hz, CH$_2$CH$_3$). $^{19}F$ NMR (1:1 $C_6D_6/C_6D_5Br$): δ −77.85. Anal. Calcd. (%) for $C_{39}H_{39}F_3NO_4PSZn$: C, 60.74; H, 5.10; N, 1.82; S, 4.16. found: C, 60.45; H, 5.05; N, 1.94; S, 4.49.

Example 5

Synthesis of the Ligand Precursor 4,6-(PPh$_2$)$_2$C$_{12}$H$_6$O (5)

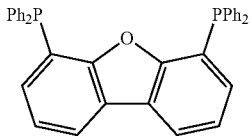

(5)

The ligand precursor, 4,6-(PPh$_2$)$_2$C$_{12}$H$_6$O was prepared as described by Kranenburg et al.[7] with several modifications. A 250 mL round-bottom flask was charged with 2.6869 g (15.974 mmol) of dibenzofuran, to which 100 mL of diethylether was added by vacuum transfer at −78° C. Tetramethylethylenediamine (TMEDA) was injected slowly (7.2 mL, 5.6 g, 48 mmol) and the suspension was allowed to warm to ambient temperature over approximately 20 min. The dibenzofuran fully dissolved to afford a light yellow solution. This solution was cooled back to −78° C. and a solution of $^{sec}$butyllithium (35 mL at 1.4 mol/L in heptane, 49 mmol) was added dropwise. The reaction mixture was stirred for 2 h producing a light green suspension which became dark green upon slow warming to ambient temperature. The reaction mixture was stirred for an additional 6 h at ambient temperature and then cooled to −78° C. Beginning 9 h after the initial injection of $^{sec}$butyllithium, 9.0 mL (11 g, 50 mmol) of neat chlorodiphenylphosphine was injected rapidly. An immediate color change from green to white was noted. The reaction mixture was gradually warmed back to ambient temperature and stirred for an additional 14 h during which a light brown suspension formed. The solvent was removed in vacuo. All subsequent manipulations were performed under aerobic conditions. The resulting light brown oil was dissolved in 80 mL of dichloromethane and quenched with 50 mL of distilled water. The aqueous phase was removed and the organic phase was washed with three subsequent 50 mL fractions of distilled water. The organic phase was dried thoroughly in vacuo and the resultant light brown oily solid was washed five times with 50 mL fractions of pentane. During each washing procedure, the mixture was sonicated and vigorously stirred for approximately 5 min prior to filtration. The resultant white solid was dried thoroughly in vacuo affording 6.06 g (11.3 mmol, 70.9%) of the desired product. $^1H$ and $^{31}P\{^1H\}$ NMR spectra matched published results.[8] $^{31}P\{^1H\}$ NMR (chloroform-d): δ −16.8 (s). $^1H$ NMR (chloroform-d): δ 7.95 (d, $^3J_{HH}$=7.5 Hz, 2H, Aromatic H), 7.35-7.20 (ov m, 22H, Aromatic H), 7.10 (m, 2H, Aromatic H).

Example 6(a)

Synthesis of the Ligand 4,6-(MesNPPh$_2$)$_2$ C$_{12}$H$_6$O (6a)

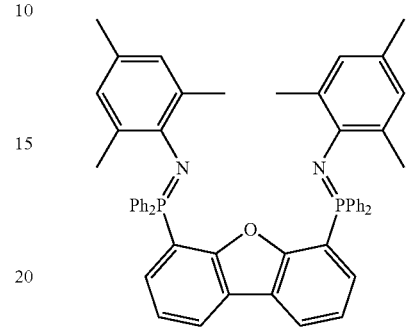

(6a)

A 500 mL teflon-sealed glass reaction vessel was charged with 5.7732 g (10.760 mmol) of precursor 4,6-(PPh$_2$)$_2$ C$_{12}$H$_6$O, (5). The precursor dissolved fully in 110 mL of toluene and then excess neat 2,4,6-trimethylphenylazide (mesityl azide, MesN$_3$)[9] (4.255 g, 26.39 mmol) was added. Evolution of a colorless gas was noted within 5 min and the solution was stirred at ambient temperature, with occasional venting, for 60 min. The temperature was then gradually raised to 65° C. and the solution was stirred for 16 h, over which time the color changed from yellow to light brown. An additional 0.459 g (2.85 mmol) of neat MesN$_3$ was added and the reaction mixture was allowed to stir at 65° C. until the $^{31}P$ NMR spectrum of crude reaction mixture aliquots indicated that the reaction had reached completion (approximately 2 additional h). The solution was cooled to ambient temperature and transferred to a 100 mL round-bottom flask in two fractions of approximately 60 mL each. The solvent was removed in vacuo between fractions and after the full volume had been transferred, yielding an oily yellow solid. All subsequent manipulations were conducted under aerobic conditions. The product was washed five times with 50 mL fractions of hexane. During each washing procedure, the mixture was sonicated and vigorously stirred for approximately 5 min prior to filtration. The product was collected as a white powder and dried in vacuo. Total yield was 93.9% (8.10 g, 10.1 mmol). $^{31}P\{^1H\}$ NMR (benzene-d$_6$): δ −17.6 (s). $^1H$ NMR (benzene-d$_6$): δ 7.82 (dd, $^3J_{PH}$=12.9 Hz, $^3J_{HH}$=7.6 Hz, 2H, Aromatic H), 7.71-7.60 (m, 8H, o-PPh$_2$), 7.57 (d, 2H, $^3J_{HH}$=7.6 Hz, Aromatic H), 6.95 (t, 2H, $^3J_{HH}$=7.6 Hz, Aromatic H), 6.92-6.82 (br ov m, 16H, m-PPh$_2$+p-PPh$_2$+m-Mes), 2.27 (s, 6H, p-Mes), 1.93 (s, 12H, o-Mes). $^{13}C\{^1H\}$ NMR (benzene-d$_6$): δ 157.0 (s), 145.2 (s), 133.0 (s), 132.7 (d, $^3J_{CP}$=7.5 Hz, m-PPh$_2$), 132.0 (d, $^2J_{CP}$=10.6 Hz, o-PPh$_2$), 131.9 (d, $^1J_{CP}$=50.6 Hz), 131.3 (d, $^2J_{CP}$=2.7 Hz), 129.0 (s), 128.6 (s, m-Mes), 127.0 (d, $^3J_{CP}$=3.0 Hz), 124.5 (d, $^2J_{CP}$=6.8 Hz, ipso-Mes), 124.0 (s, p-PPh$_2$), 123.4 (s), 121.5 (d, $^1J_{CP}$=93.6 Hz, ipso-PPh$_2$), 21.1 (s), 21.0 (s). Anal. Calcd. (%) for C$_{64}$H$_{48}$N$_2$OP$_2$: C, 80.76; H, 6.04; N, 3.48. Found: C, 80.46; H, 6.03; N, 3.49.

(b): Synthesis of the Ligand 4,6-(o-tolyl-NPPh$_2$)$_2$ C$_{12}$H$_6$O (6b)

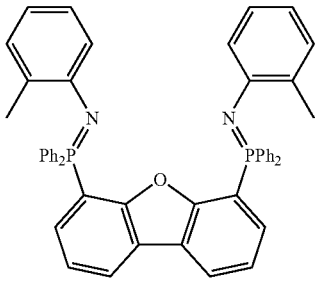

(6b)

To a solution of 4,6-(PPh$_2$)$_2$C$_{12}$H$_6$O, (5) (1.32 g, 2.46 mmol mmol) in toluene (40 mL) was added o-tolyl-azide (0.69 g, 5.2 mmol). The reaction mixture was heated to 70° C. and stirred for 19 hours. The solution was then filtered to remove any solid impurities. Toluene solvent was removed in vacuo generating an oily yellow material. Pentane (40 mL) was added and vigorously stirred, generating a light yellow suspension. The solid was collected by filtration, washed with pentane (3×10 mL), and dried in vacuo, giving a light yellow powder in 56.6% yield (1.04 g, 1.39 mmol). $^1$H NMR (C$_6$D$_6$): δ 8.27 (dd, 2H, $^3$J$_{PH}$=13.4 Hz, $^3$J$_{HH}$=7.6 Hz, Aromatic H), 7.64 (dd, 8H, $^3$J$_{PH}$=12.7 Hz, $^3$J$_{HH}$=7.4 Hz, o-Ph), 7.49 (d, 2H, $^3$J$_{HH}$=7.6 Hz, Aromatic H), 7.32 (d, 2H, $^3$J$_{HH}$=7.0 Hz, Aromatic H), 6.95 (t, 2H, $^3$J$_{HH}$=7.6 Hz, Aromatic H), 6.92-6.85 (ov m, 6H, Aromatic H), 6.81 (2H, $^3$J$_{HH}$=7.1 Hz, Aromatic H), 6.74 (td, 8H, $^3$J$_{HH}$=7.6 Hz, $^4$J$_{PH}$=2.8 Hz, m-Ph), 6.58 (d, 2H, $^3$J$_{HH}$=7.7 Hz, Aromatic H), 2.74 (s, 6H, CH$_3$). $^{31}$P{$^1$H} NMR (C$_6$D$_6$): δ −5.89. $^{13}$C{$^1$H} NMR (C$_6$D$_6$): δ 156.80 (d, J$_{CP}$=2.6 Hz), 150.30 (d, J$_{CP}$=1.0 Hz), 135.02 (d, $^2$J$_{CP}$=6.5 Hz), 133.47 (d, J$_{CP}$=22.4 Hz), 132.67 (d, $^2$J$_{CP}$=10.2 Hz, o-Ph), 131.96 (d, $^1$J$_{CP}$=106.8 Hz, ipso-Ph), 131.85 (d, $^4$J$_{CP}$=3.0 Hz, p-Ph), 131.03 (d, $^4$J$_{CP}$=2.0 Hz), 129.02 (d, $^3$J$_{CP}$=12.5 Hz, m-Ph), 126.83 (s), 125.10 (dd, J$_{CP}$=6.5 Hz, J$_{CP}$=0.9 Hz), 125.00 (d, $^4$J$_{CP}$=2.3 Hz), 124.30 (d, $^3$J$_{CP}$=10.2 Hz), 121.28 (d, $^3$J$_{CP}$=9.7 Hz), 118.52 (s), 117.52 (d, $^1$J$_{CP}$=87.4 Hz), 20.62 (s).

(c): Synthesis of the Ligand 4,6-(2-$^i$PrPh-NPPh$_2$)$_2$ C$_{12}$H$_6$O (6c)

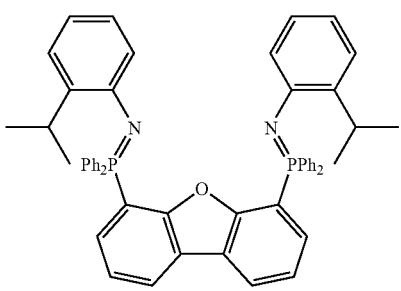

(6c)

This was prepared similarly to ligand 4,6-(o-tolyl-NPPh$_2$)$_2$ C$_{12}$H$_6$O using 4,6-(PPh$_2$)$_2$C$_{12}$H$_6$O, (5) (0.730 g, 1.36 mmol) and 2-$^i$PrPh-azide (0.46 g, 2.9 mmol), yielding the compound as a light yellow. Yield: 0.662 g, 60.6%. $^1$H NMR (C$_6$D$_6$): δ 8.26 (dd, 2H, $^3$J$_{PH}$=13.6 Hz, $^3$J$_{HH}$=6.4 Hz, Aromatic H), 7.64 (dd, 8H, $^3$J$_{PH}$=12.8 Hz, $^3$J$_{HH}$=7.0 Hz, o-Ph), 7.49 (d, 2H, $^3$J$_{HH}$=7.7 Hz, Aromatic H), 7.37 (m, 2H, Aromatic H), 7.00-6.80 (ov m, 10H, Aromatic H), 6.73 (td, 8H, $^3$J$_{HH}$=7.6 Hz, $^4$J$_{PH}$=3.0 Hz, m-Ph), 6.63 (m, 2H, Aromatic H), 4.28 (septet, 2H, $^3$J$_{HH}$=6.9 Hz, CH(CH$_3$)$_2$), 1.52 (d, 12H, $^3$J$_{HH}$=6.9 Hz, CH(CH$_3$)$_2$). $^{31}$P{$^1$H} NMR (C$_6$D$_6$): δ −5.24 (s). $^{13}$C{$^1$H}NMR (C$_6$D$_6$): δ 156.76 (d, J=2.6 Hz), 149.07 (d, J=1.1 Hz), 143.28 (d, $^2$J$_{CP}$=21.7 Hz), 135.06 (d, $^2$J$_{CP}$=6.6 Hz), 132.66 (d, $^3$J$_{CP}$=10.2 Hz, o-Ph), 131.94 (d, $^1$J$_{CP}$=107.6 Hz, ipso-Ph), 131.83 (d, $^4$J$_{CP}$=2.9 Hz, p-Ph), 129.02 (d, $^3$J$_{CP}$=12.6 Hz, m-Ph), 126.44 (s), 126.18 (d, $^4$J$_{CP}$=2.2 Hz), 125.14 (dd, J$_{CP}$=6.3 Hz, J$_{CP}$=0.9 Hz), 125.00 (d, $^4$J$_{CP}$=2.5 Hz), 124.35 (d, $^3$J$_{CP}$=9.9 Hz), 121.78 (d, $^3$J$_{CP}$=10.1 Hz), 118.90 (d, $^4$J$_{CP}$=0.5 Hz), 117.60 (d, $^1$J$_{CP}$=85.6 Hz), 29.20 (s, CH(CH$_3$)$_2$), 23.70 (s, CH(CH$_3$)$_2$).

(d): Synthesis of the Ligand 4,6-(4-$^i$PrPh-NPPh$_2$)$_2$ C$_{12}$H$_6$O (6d)

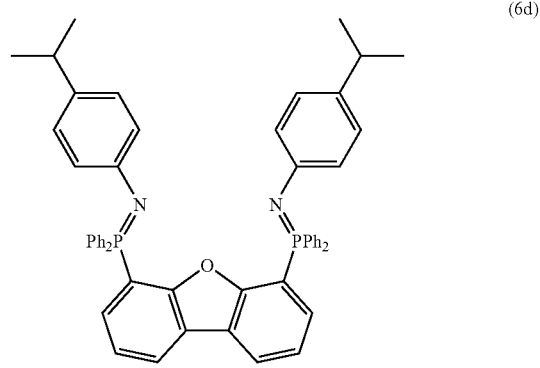

(6d)

This was prepared similarly to 4,6-(o-tolyl-NPPh$_2$)$_2$ C$_{12}$H$_6$O using 4,6-(PPh$_2$)$_2$C$_{12}$H$_6$O, (5) (0.863 g, 1.61 mmol) and 4-$^i$PrPh-azide (0.54 g, 3.3 mmol), yielding the compound as a light yellow powder. Yield: 0.737 g, 57.1%. $^1$H NMR (C$_6$D$_6$): δ 8.28 (dd, 2H, $^3$J$_{PH}$=13.7 Hz, $^3$J$_{HH}$=7.6 Hz, Aromatic H), 7.70 (dd, 8H, $^3$J$_{PH}$=12.7 Hz, $^3$J$_{HH}$=7.7 Hz, o-Ph), 7.49 (d, 2H, $^3$J$_{HH}$=7.7 Hz, Aromatic H), 7.02 (ov m, 8H, Aromatic H), 6.97-6.88 (ov m, 6H, Aromatic H), 6.86-6.77 (td, 8H, $^3$J$_{HH}$=7.7 Hz, $^4$J$_{PH}$=3.0 Hz, m-Ph), 2.73 (septet, 2H, $^3$J$_{HH}$=6.9 Hz, CH(CH$_3$)$_2$), 1.16 (d, 12H, $^3$J$_{HH}$=6.9 Hz, CH(CH$_3$)$_2$). $^{31}$P{$^1$H} NMR (C$_6$D$_6$): δ −5.10. $^{13}$C{$^1$H} NMR (C$_6$D$_6$): δ 156.86 (d, J$_{CP}$=2.2 Hz), 149.77 (d, J$_{CP}$=1.9 Hz), 138.20 (s), 135.02 (d, $^2$J$_{CP}$=7.1 Hz), 132.92 (d, $^2$J$_{CP}$=10.2 Hz, o-Ph), 131.92 (d, $^1$J$_{CP}$=104.2 Hz, ipso-Ph), 131.79 (d, $^4$J$_{CP}$=2.8 Hz, p-Ph), 129.04 (d, $^3$J$_{CP}$=12.4 Hz, m-Ph), 127.43 (s), 125.14 (dd, J$_{CP}$=5.9 Hz, J$_{CP}$=0.9 Hz), 124.90 (d, $^4$J$_{CP}$=2.4 Hz), 124.14 (d, $^3$J$_{CP}$=10.5 Hz), 124.12 (d, $^3$J$_{CP}$=17.7 Hz), 117.20 (d, $^1$J$_{CP}$=91.1 Hz), 34.13 (s, CH(CH$_3$)$_2$), 24.99 (s, CH(CH$_3$)$_2$).

(e): Synthesis of the Ligand 4,6-(Ph-NPPh$_2$)$_2$ C$_{12}$H$_6$O (6e)

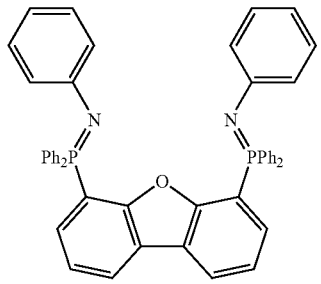

(6e)

This was prepared similarly to 4,6-(o-tolyl-NPPh$_2$)$_2$ C$_{12}$H$_6$O using 4,6-(PPh$_2$)$_2$C$_{12}$H$_6$O, (5) (0.863 g, 1.61 mmol) and phenyl-azide (0.40 g, 3.4 mmol), yielding the compound as a pale yellow powder. Yield: 0.667 g, 57.7%. $^1$H NMR (C$_6$D$_6$): δ 8.24 (dd, 2H, $^3J_{HH}$=13.9 Hz, $^3J_{HH}$=7.6 Hz, Aromatic H), 7.68 (dd, 8H, $^3J_{PH}$=12.6 Hz, $^3J_{HH}$=7.6 Hz, o-Ph), 7.48 (d, $^3J_{HH}$=7.6 Hz, Aromatic H), 7.18-7.04 (ov m, 8H, Aromatic H), 6.98-6.88 (ov m, 6H, Aromatic H), 6.87-6.75 (ov m, 10H, Aromatic H). $^{31}$P{$^1$H} NMR (C$_6$D$_6$): δ –4.17 (s). $^{13}$C{$^1$H} NMR (C$_6$D$_6$): δ 156.86 (d, J$_{CP}$=2.2 Hz), 152.08 (d, J$_{CP}$=1.9 Hz), 134.92 (d, $^2J_{CP}$=7.1 Hz), 132.92 (d, $^2J_{CP}$=10.2 Hz, o-Ph), 131.87 (d, $^4J_{CP}$=3.0 Hz, p-Ph), 131.67 (d, $^1J_{CP}$=103.7 Hz, ipso-Ph), 129.54 (d, $^4J_{CP}$=1.2 Hz, m-NPh), 129.06 (d, $^3J_{CP}$=12.4 Hz, m-Ph), 125.14 (dd, J$_{CP}$=6.4 Hz, J$_{CP}$=0.9 Hz), 124.96 (d, $^4J_{CP}$=2.5 Hz), 124.42 (d, $^3J_{PC}$=17.8 Hz, o-NPh), 124.14 (d, $^3J_{PC}$=10.4 Hz), 118.42 (d, $^5J_{PC}$=0.8 Hz, p-NPh), 116.96 (d, $^1J_{CP}$=93.0 Hz).

Example 7(a)

Synthesis of Cationic Ligand [H-4,6-(MesNPPh$_2$)$_2$ C$_{12}$H$_6$O]$^+$[B(C$_6$F$_5$)$_4$]$^+$ (7a)

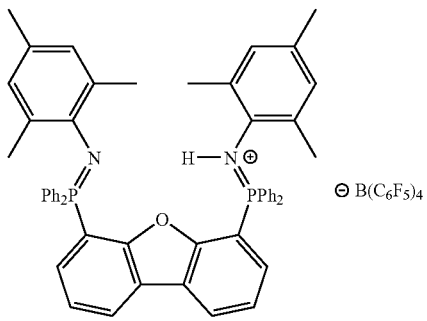

A 50 mL round-bottom flask was charged with 0.2710 g (0.3375 mmol) of 4,6-(MesNPPh$_2$)$_2$C$_{12}$H$_6$O, (6a), 0.2659 g (0.3319 mmol) of [HNMe$_2$Ph][B(C$_6$F$_6$)$_4$] and 10 mL of benzene. The solution was stirred for 10 min and the benzene was removed in vacuo affording an oily, light yellow solid containing the desired product and Me$_2$NPh. The flask was attached to a swivel frit apparatus and the solid was washed three times with 10 mL portions of pentane. During each washing procedure, the mixture was sonicated and stirred for several min before filtration. The resultant light yellow solid was dried in vacuo for 20 h. A total of 0.3945 g (0.2660 mmol) of [H-4,6-(MesN═PPh$_2$)$_2$dbf][B(C$_6$F$_5$)$_4$] was recovered as an analytically pure light yellow solid (80.1% yield). $^{31}$P{$^1$H} NMR (benzene-d$_6$): δ 10.1 (s). $^{31}$P{$^1$H} NMR (chloroform-d): δ 9.4 (s). $^1$H NMR (chloroform-d): δ 8.30 (d, $^3J_{HH}$=6.0 Hz, 2H, Aromatic H), 7.57-7.21 (br ov m, 24H, Aromatic H), 6.58 (s, 4H, m-Mes), 5.72 (br s, 1H, NH), 2.17 (s, 6H, p-Mes), 1.55 (s, 12H, o-Mes). $^{13}$C{$^1$H} NMR (chloroform-d): δ 157.2 (s), 134.6 (d, $^3J_{CP}$=5.3 Hz), 134.0 (s), 133.4 (s), 132.6 (d, $^2J_{CP}$=10.6 Hz, o-PPh$_2$), 131.2 (s), 130.0 (s, p-PPh$_2$), 129.8 (s, m-PPh$_2$), 129.5 (s, m-Mes), 127.1 (s), 125.4 (s), 124.0 (s), 123.3 (s), 20.8 (s), 20.1 (s). B(C$_6$F$_6$)$_4^-$ resonances not reported. Ipso-PPh$_2$ not observed. $^{19}$F NMR (benzene-d$_6$): δ –130.8 (br d, $^3J_{FF}$=11 Hz, 8F, o-C$_6$F$_5$), –161.7 (t, $^3J_{FF}$=22 Hz, 4F, p-C$_6$F$_5$), –165.5 (m, 8F, m-C$_6$F$_5$). $^{11}$B NMR (chloroform-d): δ –16.7 (br s). Anal. Calcd. (%) for C$_{78}$H$_{49}$BF$_{20}$N$_2$OP$_2$: C, 63.17; H, 3.34; N, 1.89. Found: C, 63.34; H, 3.37; N, 1.95.

(b): Synthesis of Cationic Ligand [H-4,6-(MesN-PPh$_2$)$_2$C$_{12}$H$_6$O]$^+$[BPh$_4$]$^-$ (7b)

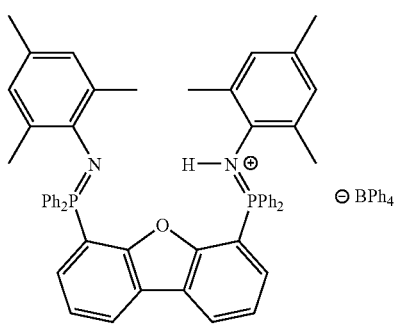

(7b)

Under aerobic conditions, two solutions: one containing 1.0531 g (1.3115 mmol) of previously prepared 4,6-(MesN-PPh$_2$)$_2$C$_{12}$H$_6$O, (6a), in 125 mL of benzene, the other containing 0.4418 g (1.291 mmol) of NaBPh$_4$ in 75 mL of distilled water, were prepared. The aqueous solution was added to the organic solution in a 500 mL round-bottom flask and the mixture was stirred vigorously for 25 min. The organic layer was decanted and washed with three 50 mL portions of distilled water. The organic layer was then thoroughly dried in vacuo for 14 h, yielding the desired product as an analytically-pure light yellow solid in high yield (1.2508 g, 1.1136 mmol, 86.26%). $^{31}$P{$^1$H} NMR (benzene-d$_6$): δ 10.1 (s). $^{31}$P{$^1$H} NMR (chloroform-d): δ 9.5 (s). $^1$H NMR (chloroform-d): δ 8.14 (d, $^3J_{HH}$=6.3 Hz, 2H, Aromatic H), 7.46-7.31 (ov m, 24H, Aromatic H), 7.30-7.19 (m, 8H, m-PPh$_2$), 6.95 (dd, $^3J_{HH}$=7.4 Hz, $^3J_{HH}$=6.1 Hz, 8H, m-BPh$_4^-$), 6.82 (t, $^3J_{HH}$=7.4 Hz, 4H, p-BPh$_4^-$), 6.58 (s, 4H, m-Mes), 5.69 (br s, 1H, NH), 2.18 (s, 6H, p-Mes), 1.56 (s, 12H, o-Mes). $^{13}$C{$^1$H} NMR (chloroform-d): δ 164.4 (1:1:1:1 q, $^1J_{CB}$=49.1 Hz, ipso-BPh$_4^-$), 157.0 (s), 136.5 (s, o-BPh$_4^-$), 134.5 (s), 133.9 (s), 133.6 (s), 132.5 (d, $^2J_{CP}$=9.8 Hz, o-PPh$_2$), 131.2 (s), 129.6 (s, p-PPh$_2$), 129.3 (s, m-PPh$_2$), 128.5 (s, m-Mes), 127.4 (s), 125.5 (s, m-BPh$_4^-$), 125.1 (s) 124.2 (d, $^2J_{CP}$=6.0 Hz), 123.4 (s), 121.6 (s, p-BPh$_4^-$), 20.8 (s), 20.2 (s). Ipso-PPh$_2$ not observed. $^{11}$B NMR (chloroform-d): δ –6.5 (br s). Anal. Calcd. (%) for C$_{78}$H$_{69}$BN$_2$OP$_2$: C, 83.39; H, 6.20; N, 2.49. Found: C, 83.24; H, 6.11; N, 2.51.

(c): Synthesis of Cationic Ligand [H-4,6-(o-tolyl-NPPh$_2$)$_2$C$_{12}$H$_6$O]$^+$[BPh$_4$]$^-$ (7c)

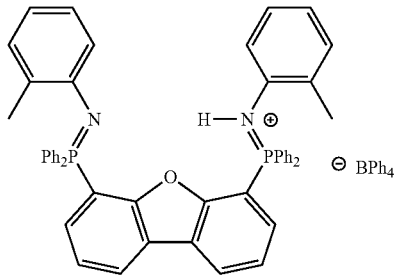

(7c)

To a suspension of 4,6-(o-tolyl-NPPh$_2$)$_2$C$_{12}$H$_6$O, (6b), (0.500 g, 0.670 mmol) in methanol (5 mL) was added 1M HCl (0.67 mL, 0.67 mmol). With stirring, sodium tetraphenylborate (0.25 g, 0.73 mmol) in a minimum of methanol was added, immediately generating a flocculent white precipitate. The precipitate was collected by filtration, washed with methanol and pentane, and dried in vacuo, yielding [H-4,6-(o-tolyl-NPPh$_2$)$_2$C$_{12}$H$_6$O]$^+$[BPh$_4$]$^-$ as a white powder in 70.4% yield (0.504 g, 0.472 mmol). $^1$H NMR (acetone-d$^6$): δ 8.70 (d, 2H, $^3J_{HH}$=7.7 Hz, Aromatic H), 7.90 (dd, 2H, $^3J_{PH}$=14.2 Hz, $^3J_{HH}$=7.7 Hz, Aromatic H), 7.72 (td, $^3J_{HH}$=7.7 Hz, $^4J_{PH}$=1.8 Hz, Aromatic H), 7.64-7.49 (ov m, 12H, Aromatic H), 7.39-7.28 (ov m, 16H, Aromatic H), 7.02 (d, 2H, $^3J_{HH}$=7.3 Hz, Aromatic H), 6.91 (t, 8H, $^3J_{HH}$=7.3 Hz, m-BPh$_4$), 6.81-6.72 (ov m, 6H, Aromatic H), 6.67 (t, 2H, $^3J_{HH}$=7.5 Hz, Aromatic H), 6.42 (d, 2H, $^3J_{HH}$=7.7 Hz, Aromatic H), 2.14 (s, 6H, CH$_3$); $^{31}$P{$^1$H} NMR (acetone-d$^6$): δ 12.6 (br s). $^{13}$C{$^1$H} NMR (acetone-d$^6$): δ 165.00 (q, $^1J_{BC}$=49.4 Hz, ipso-BPh$_4$), 157.78 (d, J$_{CP}$=2.2 Hz), 142.18 (br s), 137.10 (q, $^2J_{BC}$=1.4 Hz, o-BPh$_4$), 135.21 (d, $^2J_{CP}$=7.6 Hz), 134.60 (d, $^4J_{CP}$=2.1 Hz, p-Ph), 133.66 (d, $^2J_{CP}$=10.8 Hz, o-Ph), 131.39 (s), 130.18 (d, $^3J_{CP}$=13.1 Hz, m-Ph), 128.61 (s), 127.19 (d, $^4J_{CP}$=1.3 Hz), 126.05 (q, $^3J_{CP}$=2.8 Hz, m-BPh$_4$), 125.88 (d, $^3J_{CP}$=10.6 Hz), 125.80 (dd, J$_{CP}$=6.6 Hz, J$_{CP}$=1.1 Hz), 124.87 (br s), 123.36 (br s), 122.30 (s, p-BPh$_4$), 19.31 (s), 3 quaternary carbons were not observed. $^{11}$B{$^1$H} NMR (acetone-d$^6$): −6.50.

(d): Synthesis of Cationic Ligand [H-4,6-(2-$^i$Pr—N—PPh$_2$)$_2$C$_{12}$H$_6$O]$^+$[BPh$_4$]$^-$ (7d)

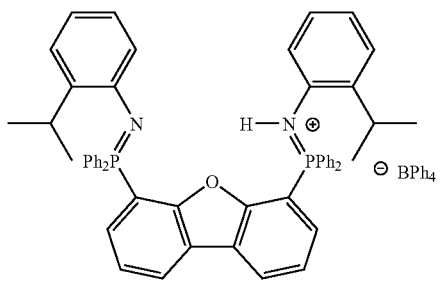

(7d)

This was prepared similarly to [H-4,6-(o-tolyl-NPPh$_2$)$_2$C$_{12}$H$_6$O]$^+$[BPh$_4$]$^-$ from 4,6-(2-$^i$Pr—N—PPh$_2$)$_2$C$_{12}$H$_6$O, (6c), (0.50 g, 0.62 mmol), 1M HCl (0.62 mL, 0.62 mmol), and sodium tetraphenylborate (234 mL, 0.68 mmol). A white powder was obtained in 63% yield (0.44 g, 0.39 mmol). $^1$H NMR (acetone-d$^6$): δ 8.72 (d, 2H, $^3J_{HH}$=7.7 Hz, Aromatic H), 8.00 (dd, 2H, $^3J_{PH}$=13.6 Hz, $^3J_{HH}$=7.7 Hz, Aromatic H), 7.78 (t, 2H, $^3J_{HH}$=7.7 Hz, Aromatic H), 7.60-7.46 (ov m, 14H, Aromatic H), 7.40-7.25 (ov m, 16H, Aromatic H), 7.14 (d, 2H, $^3J_{HH}$=7.5 Hz, Aromatic H), 6.91 (t, 8H, $^3J_{HH}$=7.4 Hz, m-BPh$_4$), 6.85 (t, 2H, $^3J_{HH}$=7.5 Hz, Aromatic H), 6.76 (t, 4H, $^3J_{HH}$=7.2 Hz, p-BPh$_4$), 6.63 (t, 2H, $^3J_{HH}$=7.5 Hz, Aromatic H), 6.48 (d, 2H, $^3J_{HH}$=7.9 Hz, Aromatic H); $^{31}$P{$^1$H} NMR (acetone-d$^6$): δ 13.7 (br s). $^{13}$C{$^1$H} NMR (acetone-d$^6$): δ 165.00 (q, $^1J_{BC}$=49.4 Hz, ipso-BPh$_4$), 157.70 (d, J$_{PC}$=2.8 Hz), 145.24 (d, J$_{PC}$=11.7 Hz), 137.10 (q, $^2J_{BC}$=1.4 Hz, o-BPh$_4$), 135.06 (d, $^2J_{PC}$=6.8 Hz), 134.80 (br s, p-Ph), 133.65 (d, $^2J_{PC}$=10.8 Hz, o-Ph), 130.29 (d, $^3J_{PC}$=13.1 Hz, m-Ph), 128.88 (br s), 126.94 (d, $^4J_{PC}$=1.3 Hz), 126.85 (br s), 126.20 (br s), 126.07 (q, $^3J_{BC}$=2.8 Hz, m-BPh$_4$), 125.84 (dd, J$_{PC}$=6.8 Hz, J$_{CP}$=1.1 Hz), 125.25 (br s), 124.24 (br s), 122.30 (s, p-BPh$_4$), 28.61 (s, CH(CH$_3$)$_2$), 23.41 (s, CH(CH$_3$)$_2$), 3 quaternary carbons are not observed. $^{11}$B{$^1$H} NMR (acetone-d$^6$): δ −6.49.

(e): Synthesis of Cationic Ligand [H-4,6-(4-$^i$Pr—N—PPh$_2$)$_2$C$_{12}$H$_6$O]$^+$[BPh$_4$]$^-$ (7e)

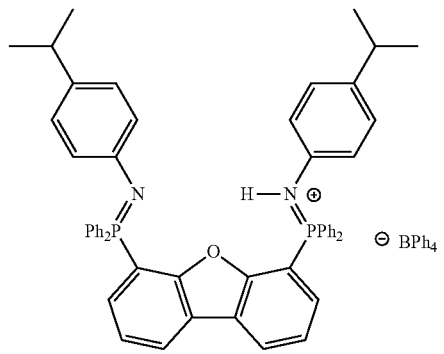

(7e)

This was prepared similarly to [H-4,6-(o-tolyl-NPPh$_2$)$_2$C$_{12}$H$_6$O]$^+$[BPh$_4$]$^-$ from 4,6-(4-$^i$Pr—N—PPh$_2$)$_2$C$_{12}$H$_6$O, (6d), (0.50 g, 6.2 mmol), 1M HCl (0.62 mL, 6.2 mmol), and sodium tetraphenylborate (0.23 g, 0.67 mmol). A white powder was obtained in 84% yield (0.58 g, 0.52 mmol). $^1$H NMR (acetone-d$^6$): δ 8.66 (d, 2H, $^3J_{HH}$=7.7 Hz, Aromatic H), 7.86 (dd, 2H, $^3J_{PH}$=14.0 Hz, $^3J_{HH}$=7.7 Hz, Aromatic H), 7.78-7.64 (ov m, 10H, Aromatic H), 7.60 (t, 4H, J$_{HH}$=7.6 Hz, p-Ph), 7.43 (td, 8H, $^3J_{HH}$=7.6 Hz, $^4J_{PH}$=3.4 Hz, m-Ph), 7.34 (br s, o-BPh$_4$), 6.97-6.84 (ov m, 12H, Aromatic H), 6.80-6.70 (ov m, 8H, Aromatic H), 2.75 (septet, 2H, $^3J_{HH}$=6.9 Hz, CH(CH$_3$)$_2$), 1.13 (d, 12H, $^3J_{HH}$=6.9 Hz, CH(CH$_3$)$_2$). $^{31}$P{$^1$H} NMR (acetone-d$^6$): δ 14.24 (br s). $^{11}$B NMR (acetone-d$^6$): δ −6.50. $^{13}$C{$^1$H} NMR (acetone-d$^6$): δ 165.00 (q, $^1J_{CB}$=49.4 Hz, ipso-BPh$_4$), 157.54 (d, J=2.2 Hz), 142.34 (s), 142.27 (s), 137.11 (q, $^2J_{CB}$=1.4 Hz, o-BPh$_4$), 134.85 (d, $^4J_{CP}$=2.8 Hz, p-Ph), 134.74 (d, $^2J_{CP}$=8.0 Hz), 133.90 (d, $^2J_{CP}$=11.0 Hz, o-Ph), 130.48 (d, $^3J_{CP}$=13.2 Hz, m-Ph), 128.68 (d, $^4J_{CP}$=2.8 Hz), 127.71 (s), 126.06 (q, $^3J_{CB}$=2.8 Hz, m-BPh$_4$), 125.86 (d, $^3J_{CP}$=11.4 Hz), 125.82 (dd, J$_{PH}$=6.8 Hz, J$_{CP}$=1.1 Hz), 124.54 (br s), 123.34 (d, $^3J_{CP}$=11.6 Hz), 122.31 (s, p-BPh$_4$), 111.34 (d, J$_{CP}$=4.2 Hz), 34.03 (s, CH(CH$_3$)$_2$), 24.47 (s, CH(CH$_3$)$_2$).

(f): Synthesis of Cationic Ligand [H-4,6-(Ph-N—PPh$_2$)$_2$C$_{12}$H$_6$O]$^+$[BPh$_4$]$^-$ (7f)

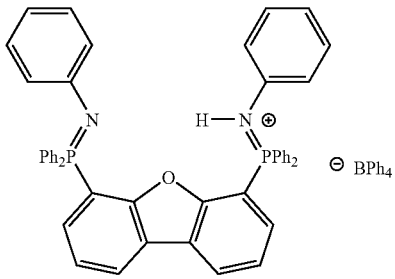

This was prepared similarly to [H-4,6-(o-tolyl-NPPh$_2$)$_2$C$_{12}$H$_6$O]$^+$[BPh$_4$]$^-$ from 4,6-(Ph-N—PPh$_2$)$_2$C$_{12}$H$_6$O, (6e), (0.50 g, 7.0 mmol), 1M HCl (0.70 mL, 7.0 mmol), and sodium tetraphenylborate (0.24 g, 0.70 mmol). The compound was obtained as a white powder in 76% yield (0.55 g, 5.3 mmol). $^1$H NMR (acetone-d$^6$): δ 8.67 (d, 2H, $^3J_{HH}$=7.7 Hz, Aromatic H), 7.90 (dd, 2H, $^3J_{PH}$=14.2 Hz, $^3J_{HH}$=7.7 Hz, Aromatic H), 7.78-7.64 (om, 10H, Aromatic H), 7.59 (t, 4H, $^3J_{HH}$=7.1 Hz, Aromatic H), 7.44 (td, 8H, $^3J_{HH}$=7.5 Hz, $^4J_{PH}$=3.5 Hz, m-Ph), 7.35 (m, 8H, o-BPh$_4$), 7.02 (t, 4H, $^3J_{HH}$=7.5 Hz, m-NPh), 6.91 (t, 4H, $^3J_{HH}$=7.3 Hz, m-BPh$_4$), 6.82 (t, 2H, $^3J_{HH}$=7.5 Hz, p-NPh), 6.80-6.70 (ov m, 8H, p-BPh$_4$+o-NPh). $^{31}$P{$^1$H} NMR (acetone-d$^6$): δ 14.53 (br s). $^{13}$C{$^1$H} NMR (acetone-d$^6$): δ 165.00 (q, $^1J_{BC}$=49.4 Hz), 157.50 (d, J$_{PC}$=2.4 Hz), 144.77 (s), 137.10 (q, J$_{BC}$=1.4 Hz, o-BPh$_4$), 134.91 (d, J$_{PC}$=3.0 Hz, p-Ph), 134.76 (d, J$_{PC}$=7.8 Hz), 133.86 (d, $^2$J$_{PC}$=11.0 Hz, o-Ph), 130.50 (d, $^3$J$_{PC}$=13.2 Hz, m-Ph), 129.90 (d, $^4$J$_{PC}$=0.5 Hz, m-NPh), 128.76 (d, $^4$J$_{PC}$=2.6 Hz), 126.06 (q, $^3$J$_{BC}$=2.8 Hz, m-BPh$_4$), 125.89 (s), 125.79 (dd, J$_{PC}$=6.8 Hz, J$_{PC}$=1.1 Hz), 125.06 (d, $^1$J$_{PC}$=105.6 Hz, ipso-Ph), 123.39 (d, $^3$J$_{PC}$=11.7 Hz, o-NPh), 122.31 (s, p-BPh$_4$), 122.06 (s), 111.22 (d, $^1$J$_{PC}$=97.8 Hz). $^{11}$B NMR (acetone-d$^6$): δ −6.50.

Example 8

Synthesis of Cationic Ligand [H$_2$-4,6-(MesNPPh$_2$)$_2$C$_{12}$H$_6$O]$^+$[BPh$_4$]$_2^-$ (8)

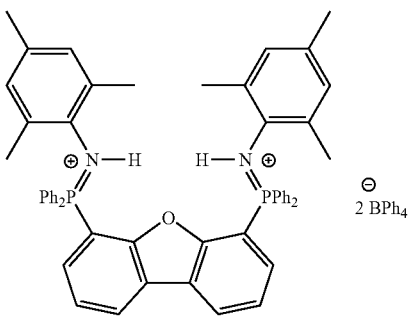

An excess of 1M aqueous HCl (0.50 mL, 0.50 mmol) was added to a suspension of 4,6-(MesNPPh$_2$)$_2$C$_{12}$H$_6$O, (6a), (0.110 g, 0.137 mmol) in methanol (5 mL). With stirring, a slight excess of NaBPh$_4$ (0.112 g, 0.327 mmol) in MeOH (5 mL) was added, immediately yielding a fluffy white precipitate. Stirring was continued for another 5 min. The precipitate was collected by filtration, washed three times with methanol, and dried in vacuo to give the product in 91.2% yield (0.170 g, 0.125 mmol). $^{31}$P{$^1$H} NMR (acetone-d$^6$): δ 28.1 (s). $^1$H NMR (acetone-d$^6$): δ 8.56 (d, 2H, $^3J_{HH}$=7.8 Hz, Aromatic H), 8.14 (d, 2H, $^3J_{HP}$=9.7 Hz, NH), 8.08 (dd, 2H, $^3J_{HP}$=14.3 Hz, $^3J_{HH}$=7.8 Hz, Aromatic H), 7.61 (td, 2H, $^3J_{HH}$=7.8 Hz, $^4J_{HP}$=1.4 Hz, Aromatic H), 7.06 (t, 4H, $^3J_{HH}$=7.4 Hz, p-PPh$_2$), 6.84 (td, 8H, $^3J_{HH}$=7.8 Hz, $^4J_{HH}$=3.8 Hz, m-PPh$_2$), 6.78-6.65 (m, 24H, o-BPh$_4^-$+o-PPh$_2$), 6.47 (t, 16H, $^3J_{HH}$=7.2 Hz, m-BPh$_4^-$), 6.33 (t, 8H, $^3J_{HH}$=7.2 Hz, p-BPh$_4^-$), 6.22 (s, 4H, m-Mes), 1.63 (s, 6H, p-Mes), 1.26 (s, 12H, o-Mes). $^{13}$C NMR (acetone-d$^6$) 165.0 (1:1:1:1 q, $^1J_{CB}$=49.4 Hz, ipso-BPh$_4^-$), 157.6 (d, J$_{CP}$=3.4 Hz), 138.2 (s), 137.1 (1:1:1:1 q, $^2$J$_{CB}$=1.4 Hz, o-BPh$_4^-$), 137.0 (br s), 135.0 (s), 134.3 (d, J$_{CP}$=11.4 Hz), 132.6 (s), 131.1 (s), 130.9 (s), 130.7 (d, J$_{CP}$=1.9 Hz), 130.3 (s), 129.8 (s), 127.8 (s), 127.0 (d, J$_{CP}$=11.7 Hz), 126.1 (1:1:1:1 q, $^3$J$_{CP}$=2.8 Hz, m-BPh$_4^-$), 122.3 (1:1:1:1 q, $^4$J$_{CB}$=0.5 Hz, p-BPh$_4^-$), 116.1 (s), 20.8 (s), 19.8 (s). $^{11}$B NMR (acetone-d$^6$): δ −6.5 (br s) Anal. Calcd. (%) for C$_{102}$H$_{90}$B$_2$N$_2$OP$_2$·C$_3$H$_6$O: C, 83.99; H, 6.44; N, 1.87. Found: C, 83.89; H, 6.19; N, 1.94.

Example 9(a)

Synthesis of Catalyst [4,6-(MesN=PPh$_2$)$_2$C$_{12}$H$_6$O.MgBu][B(C$_6$F$_5$)$_4$] (9a)

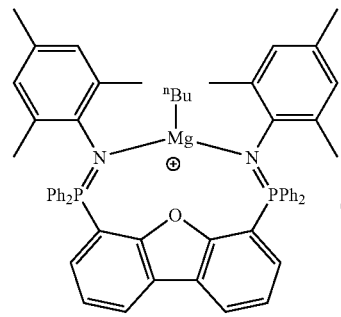

Under argon, a 50 mL round-bottom flask was charged with 0.1791 g (0.1207 mmol) of [H-4,6-(MesNPPh$_2$)$_2$C$_{12}$H$_6$O]$^+$[B(C$_6$F$_5$)$_4$]$^-$, (7a), to which 12 mL of benzene was added. di($^n$butyl)magnesium (0.112 mL of 1.0 M solution in heptane, 0.11 mmol) was slowly injected and evolution of a colorless gas was noted. The solution was stirred for 50 min then benzene was removed in vacuo. This afforded the desired product as a pale yellow solid in 73% yield (0.1286 g, 0.08226 mmol). $^{31}$P{$^1$H} NMR (benzene-d$^6$): δ 23.0 (s). $^1$H NMR (benzene-d$^6$): δ 7.80 (d, $^3J_{HH}$=6.0 Hz, 2H, Aromatic H), 7.28 (dd, $^3J_{HP}$=12 Hz, $^3J_{HH}$=9.2 Hz, 8H, o-PPh$_2$), 7.09-6.97 (br ov m, 6H, Aromatic H), 6.97-6.80 (br ov m, 10H, Aromatic H), 6.36 (s, 4H, m-Mes), 2.04 (s, 6H, p-Mes), 1.50 (s, 12H, o-Mes), 1.38-1.32 (ov m, 4H, MgCH$_2$CH$_2$CH$_2$CH$_3$), 0.99 (t, $^3J_{HH}$=7.3 Hz, 3H, MgCH$_2$CH$_2$CH$_2$CH$_3$), −0.13 (t, $^3J_{HH}$=9.2

Hz, 2H, MgCH$_2$CH$_2$CH$_2$CH$_3$). $^{13}$C{$^1$H} NMR (benzene-d$_6$): δ 156.8 (s), 137.3 (s), 135.6 (d, $^2J_{CP}$=6.8 Hz), 134.1 (d, $^2J_{CP}$=9.1 Hz, o-PPh$_2$), 133.9 (s), 133.7 (d, $^1J_{CP}$=45.5 Hz), 133.1 (d, $^2J_{CP}$=9.8 Hz), 130.0 (s, m-Mes), 129.6 (s), 129.4 (s), 128.1 (s), 126.4 (s), 125.3 (d, J$_{CP}$=8.3 Hz), 112.7 (d, $^1J_{CP}$=106 Hz, ipso-PPh$_2$), 32.0, 30.2 (s, MgCH$_2$CH$_2$CH$_2$CH$_3$), 20.6 (s), 20.1 (s), 14.1 (s, MgCH$_2$CH$_2$CH$_2$CH$_3$), 12.0 (s, MgCH$_2$CH$_2$CH$_2$CH$_3$). B(C$_6$F$_5$)$_4^-$ resonances not reported. $^{19}$F NMR (benzene-d$_6$): δ −130.7 (d, $^3J_{FF}$=11 Hz, 8F, o-C$_6$F$_5$), −161.7 (t, $^3J_{FF}$=22 Hz, 4F, p-C$_6$F$_5$), −165.5 (m, 8F, m-C$_6$F$_5$). $^{11}$B NMR (benzene-d$_6$): δ −15.8 (br s). Anal. Calcd. (%) for C$_{82}$H$_{57}$BF$_{20}$MgN$_2$OP$_2$: C, 62.99; H, 3.68; N, 1.79. Found: C, 62.17; H, 3.86; N, 1.84.

(b): Synthesis of Catalyst [4,6-(MesN=PPh$_2$)$_2$ C$_{12}$H$_6$O.MgBu][BPh$_4$] (9b)

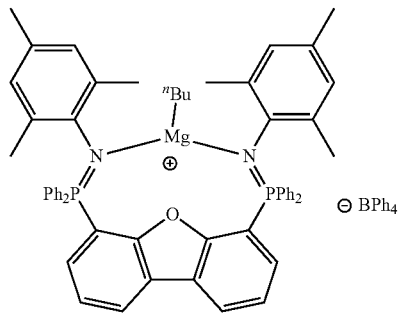

(9b)

Under argon, a 100 mL round-bottom flask was charged with 0.7422 g (0.6608 mmol) of [H-4,6-(MesNPPh$_2$)$_2$ C$_{12}$H$_6$O]$^+$[BPh$_4$]$^-$, (7b), to which 40 mL of benzene was added. A solution of di($^n$butyl)magnesium (0.67 mL of 1.0 M solution in heptane, 0.67 mmol) in 4 mL of benzene was slowly injected. Evolution of a gas was noted, followed by a color change from yellow to pale pink as the reaction mixture was stirred for 30 min at ambient temperature. The solvent was removed in vacuo yielding the desired material as a white solid (0.7242 g, 0.6017 mmol, 91.07%). $^{31}$P{$^1$H} NMR (benzene-d$_6$): δ 23.2 (s). $^1$H NMR (benzene-d$_6$): δ 8.09-8.01 (br m, 8H, o-BPh$_4^-$) 7.64 (d, $^3J_{HH}$=6.0 Hz, 2H, Aromatic H), 7.26 (dd, $^3J_{HP}$=12 Hz, $^3J_{HH}$=9.1 Hz, 8H, o-PPh$_2$), 7.19 (ov t, $^3J_{HH}$=7.4 Hz, 4H, p-BPh$_4^-$), 7.09-6.97 (br ov m, 14H, Aromatic H), 6.97-6.84 (br ov m, 10H, Aromatic H), 6.35 (s, 4H, m-Mes), 2.03 (s, 6H, p-Mes), 1.52 (s, 12H, o-Mes), 1.38-1.32 (ov m, 4H, MgCH$_2$CH$_2$CH$_2$CH$_3$), 0.99 (t, $^3J_{HH}$=7.3 Hz, 3H, MgCH$_2$CH$_2$CH$_2$CH$_3$), −0.13 (t, $^3J_{HH}$=9.2 Hz, 2H, MgCH$_2$CH$_2$CH$_2$CH$_3$). $^{13}$C{$^1$H} NMR (benzene-d$_6$): δ 165.4 (1:1:1:1 q, $^1J_{CB}$=48.3 Hz, ipso-BPh$_4^-$), 156.6 (s), 137.5 (s, o-BPh$_4^-$), 137.2 (s), 135.7 (d, $^2J_{CP}$=6.8 Hz), 133.9 (ov, o-PPh$_2$), 133.8 (s), 133.1 (d, $^2J_{CP}$=9.1 Hz), 129.9 (s, m-Mes), 129.7 (s), 129.5 (s), 128.1 (s), 126.5 (s), 126.2 (s, m-BPh$_4^-$), 125.4 (d, J$_{CP}$=8.3 Hz), 122.2 (s, p-BPh$_4^-$), 112.2 (d, $^1J_{CP}$=107 Hz, ipso-Ph), 32.0, 30.2 (s, MgCH$_2$CH$_2$CH$_2$CH$_3$), 20.6 (s), 20.3 (s), 14.0 (s, MgCH$_2$CH$_2$CH$_2$CH$_3$), 11.9 (s, MgCH$_2$CH$_2$CH$_2$CH$_3$). $^{11}$B NMR (benzene-d$_6$): δ −5.6 (br s). Anal. Calcd. (%) for C$_{82}$H$_{77}$BMgN$_2$OP$_2$: C, 81.81; H, 6.46; N, 2.33. Found: C, 80.85; H, 6.33; N, 2.72.

(c): Synthesis of Catalyst [4,6-(MesN=PPh$_2$)$_2$ C$_{12}$H$_6$O.ZnMe][B(C$_6$F$_5$)$_4$] (9c)

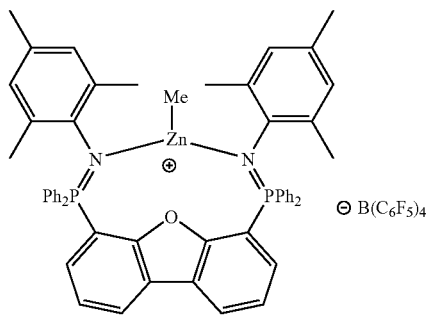

(9c)

An excess of 1.2 M dimethylzinc in toluene (65 μL, 0.0780 mmol) was added to a solution of [H-4,6-(MesN=PPh$_2$)$_2$C$_{12}$H$_6$O]$^+$[B(C$_6$F$_5$)$_4$], (7a), (100 mg, 0.0674 mmol) in bromobenzene (2 mL). Effervescence of methane was immediately observed. After allowing the mixture to stand for 30 min at ambient temperature, the product was precipitated as a red/orange oil by addition of pentane (5 mL). The mother liquor was decanted, the resulting oil was washed twice with 1 mL of pentane, then once with 2 mL of a 1:2 benzene/pentane mixture and dried in vacuo, giving the material as a pale yellow powder in 92.0% yield (96.6 mg, 0.0618 mmol). $^1$H NMR (C$_6$D$_5$Br): δ 7.87 (d, 2H, $^3J_{HH}$=7.6 Hz, Aromatic H), 7.32-7.19 (ov m, 4H, p-Ph obscured by solvent), 7.19-7.06 (ov m, 10H, Aromatic H), 6.99 (td, 8H, $^3J_{HH}$=7.6 Hz, $^4J_{PH}$=3.2 Hz, m-Ph), 6.77 (dd, 2H, $^3J_{PH}$=11.8 Hz, $^3J_{HH}$=7.6 Hz, Aromatic H), 6.41 (s, 4H, Aromatic H), 2.05 (s, 6H, p-CH$_3$), 1.34 (s, 12H, o-CH$_3$), −0.48 (s, 3H, CH$_3$Zn); $^{11}$B{$^1$H} NMR (C$_6$D$_5$Br): δ −17.7; $^{19}$F NMR (C$_6$D$_5$Br): δ 133.22 (d, 8F, o-C$_6$F$_5$), 163.68 (t, 4F, p-C$_6$F$_5$), 167.47 (t, 8F, m-C$_6$F$_5$); $^{31}$P{$^1$H} NMR (C$_6$D$_5$Br): δ 23.4 (s). $^{13}$C{$^1$H} NMR (C$_6$D$_5$Br): δ 157.60 (s, aromatic C), 150.23 (br s, C$_6$F$_5$), 147.06 (br s, C$_6$F$_5$), 139.99 (br s, C$_6$F$_5$), 138.29 (d, J$_{PC}$=7.9 Hz, aromatic C), 136.55 (d, J$_{PC}$=6.0 Hz, aromatic C), 135.00 (br s, C$_6$F$_5$), 134.39 (d, J$_{PC}$=4.1 Hz, aromatic C), 134.12 (d, $^4J_{CP}$=2.6 Hz, p-Ph), 132.84 (d, $^2J_{CP}$=10.0 Hz, o-Ph), 132.36 (d, $^2J_{CP}$=6.8 Hz), 129.81 (s), 129.49 (d, $^3J_{CP}$=12.4 Hz, m-Ph), 127.13 (d, $^4J_{CP}$=2.3 Hz), 124.09 (d, $^3J_{CP}$=10.5 Hz), 123.96 (d, J$_{CP}$=8.9 Hz, aromatic C), 114.75 (d, $^1J_{PC}$=92.0 Hz), 20.75 (s, p-CH$_3$), 19.04 (s, o-CH$_3$). ipso-Ph not observed. Anal. Calcd. (%) for C$_{79}$H$_{51}$BF$_{20}$N$_2$OP$_2$Zn: C, 60.73; H, 3.29; N, 1.79. found: C, 59.44; H, 3.29; N, 1.71.

(d): Synthesis of Catalyst [4,6-(MesN=PPh$_2$)$_2$ C$_{12}$H$_6$O.ZnOAc][BPh$_4$] (9d)

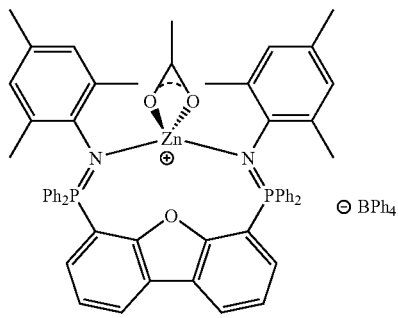

(9d)

[4,6-(MesN=PPh$_2$)$_2$C$_{12}$H$_6$O.ZnOAc][BPh$_4$] was prepared similarly to [4,6-(MesN=PPh$_2$)$_2$C$_{12}$H$_6$O.ZnMe][B(C$_6$F$_5$)$_4$], by reaction of [H-4,6-(MesN=PPh$_2$)$_2$C$_{12}$H$_6$O]$^+$[BPh$_4$]$^-$, (7b), (200 mg, 0.178 mmol) and MeZnOAc (25 mg, 0.179 mmol). After combining the reagents in bromobenzene (1 mL), the resulting cloudy solution promptly clarified to give a yellow solution. After standing for 15 min at ambient temperature the product crystallized. The mother liquor was decanted, the white crystalline material was washed with benzene and pentane, and after drying under vacuum for 24 hours, [4,6-(MesN=PPh$_2$)$_2$C$_{12}$H$_6$O.ZnOAc][BPh$_4$] was isolated in 99% yield (220 mg, 0.176 mmol). $^1$H NMR (C$_6$D$_5$Br): δ 7.83 (br s, 8H, o-BPh$_4$), 7.68 (d, 2H, $^3J_{HH}$=7.9 Hz, Aromatic H), 7.27-7.09 (m, 12H, Aromatic H), 7.05 (t, 8H, $^3J_{HH}$=7.3 Hz, m-BPh$_4$), 7.01-6.93 (m, 10H, Aromatic H), 6.93-6.84 (m, 4H, p-BPh$_4$, partially obscured by solvent), 6.71 (dd, 2H, $^3J_{PH}$=12.2 Hz, $^3J_{HH}$=7.9 Hz, Aromatic H), 6.41 (s, 4H, Aromatic H), 1.97 (d, 6H, $^4J_{HH}$=2.0 Hz, Aromatic H), 1.80 (s, 3H, CO$_2$CH$_3$), 1.40 (s, 12H, o-CH$_3$). $^{31}$P{$^1$H} NMR (C$_6$D$_5$Br): δ 28.34. $^{11}$B{$^1$H} NMR (C$_6$D$_5$Br): δ −5.55. $^{13}$C{$^1$H} NMR (C$_6$D$_5$Br): δ 185.02 (s, CO$_2$CH$_3$), 164.80 (q, $^1J_{BC}$=49.2 Hz, ipso-BPh$_4$), 138.46 (d, J$_{CP}$=8.0 Hz, aromatic C), 136.89 (q, $^2J_{BC}$=1.3 Hz, o-BPh$_4$), 136.42 (d, J$_{CP}$=5.7 Hz, aromatic C), 134.66 (d, J$_{CP}$=3.8 Hz, aromatic C), 134.26 (s, p-Ph), 133.41 (d, $^3J_{CP}$=10.3 Hz, m-Ph), 132.38 (d, $^2J_{CP}$=10.4 Hz), 131.45 (d, obscured by solvent, o-Ph), 130.04 (s), 129.44 (d, $^3J_{CP}$=12.9 Hz, m-Ph), 128.27 (s), 125.86 (q, $^3J_{BC}$=2.7 Hz, m-BPh$_4$), 121.93 (s, p-BPh$_4$), 113.76 (d, $^1J_{PC}$=92.6 Hz), 21.20 (s, CO$_2$CH$_3$), 20.80 (s, p-CH$_3$), 18.59 (s, o-CH$_3$). Signals for four quaternary carbons were not observed. Anal. Calcd. (%) for C$_{80}$H$_{71}$BN$_2$O$_3$P$_2$Zn.C$_6$H$_5$Br: C, 73.59; H, 5.46; N, 2.25. found: C, 74.66; H, 5.60; N, 2.27.

(e): Synthesis of Catalyst [4,6-(2-$^i$PrPh-N=PPh$_2$)$_2$ C$_{12}$H$_6$O.ZnMe][BPh$_4$] (9e)

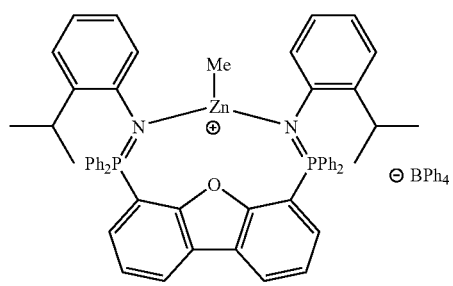

(9e)

This was prepared similarly to [4,6-(MesN=PPh$_2$)$_2$C$_{12}$H$_6$O.ZnMe][B(C$_6$F$_5$)$_4$] from [H-4,6-(2-$^i$PrPh-N=PPh$_2$)$_2$ C$_{12}$H$_6$O]$^+$[BPh$_4$]$^-$, (7b), (200 mg, 0.178 mmol) and dimethylzinc (1.2 M in toluene, 165 μL, 0.198 mmol), giving the compound in quantitative yield (214 mg, 0.178 mmol). $^{31}$P{$^1$H} NMR (C$_6$D$_5$Br+C$_6$D$_6$): δ 23.10.

Example 10

Polymerization of L-Lactide Using Catalysts of the Disclosure

Polymerization experiments were performed on an NMR scale in 1:1 C$_6$D$_6$/C$_6$D$_5$Br solvent and conversions were determined by integration of the lactide $^1$H NMR methine resonance. With an initial 1 M concentration of L-lactide and a 1% catalyst loading of (4a), gave 90% conversion to polymer after 6 hours at 100° C., while catalyst (4b) required 9 hours to reach 85% conversion under the same conditions.

Example 11

ε-Caprolactone Polymerization Using Catalysts of the Disclosure

An NMR tube was charged with 0.00083 mmol of the catalyst of selection to which 2.2 mL of benzene-d$_6$ was added. The tube was capped with a rubber NMR tube septum which was then wrapped in parafilm and shaken vigorously. Dry, distilled ε-caprolactone (48 μL, 0.43 mmol, 5.2×10$^2$ equiv.) was measured under an inert atmosphere into a 100.0 μL gastight microsyringe which was sealed by inserting the needle into a rubber septum until immediately before addition to the catalyst. Prior to monomer injection, all appropriate instrumental parameters were set and NMR spectra of the catalyst were collected. The sample was then removed from the instrument, injected with the monomer, shaken, and reinserted into the NMR spectrometer. Collection of NMR data began within 60 s of injection of the monomer. Conversion percentages were determined by integration of the most downfield methylene resonance (–COOCH$_2$–) of the polymer ($^1$H NMR (benzene-d$_6$): δ 3.98 (t, $^3J_{HH}$=6.1 Hz, 2H)) relative to those of the residual monomer ($^1$H NMR (benzene-d$_6$): δ 3.59 (t, $^3J_{HH}$=6.1 Hz, 2H)), as these resonances were most clearly resolved from all other monomer, polymer, catalyst, and residual solvent resonances. Polymerization reactions at low temperature (−40° C. to 0° C.) were performed by allowing the catalyst solution to equilibrate within the pre-cooled instrument for 20 min prior to monomer injection. Low temperature reactions were run in toluene-d$_8$ rather than benzene-d$_6$. Results are shown in Table 1.

Example 12

X-ray Crystallography of

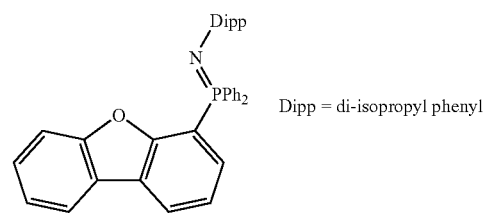

Dipp = di-isopropyl phenyl

X-ray quality single crystals of the ligand were readily obtained and its molecular structure was determined crystallographically as seen in FIG. 1.

Discussion

The ligand binding geometry can be roughly defined by measurement of two torsion angles, which measure the rotation about the P1-C2 and P1-N1 bonds. An ideal 6-membered chelate ring would have C1-C2-P1-N1 and C2-P1-N1-C25 torsion angles of 0° and 180°, respectively. The solid state structure of the free ligand, however, exhibits corresponding torsion angles of 167.95(19)° and 155.71(19)°. The significant rotation about the C2-P1 bond is likely a result of steric interactions between the dibenzofuran backbone and the bulky Dipp group of the phosphinimine functionality.

Example 13

X-ray Crystallography of

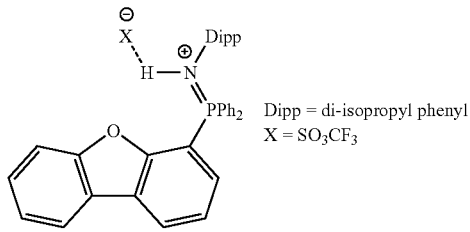

Dipp = di-isopropyl phenyl
X = SO$_3$CF$_3$

Figure 2:
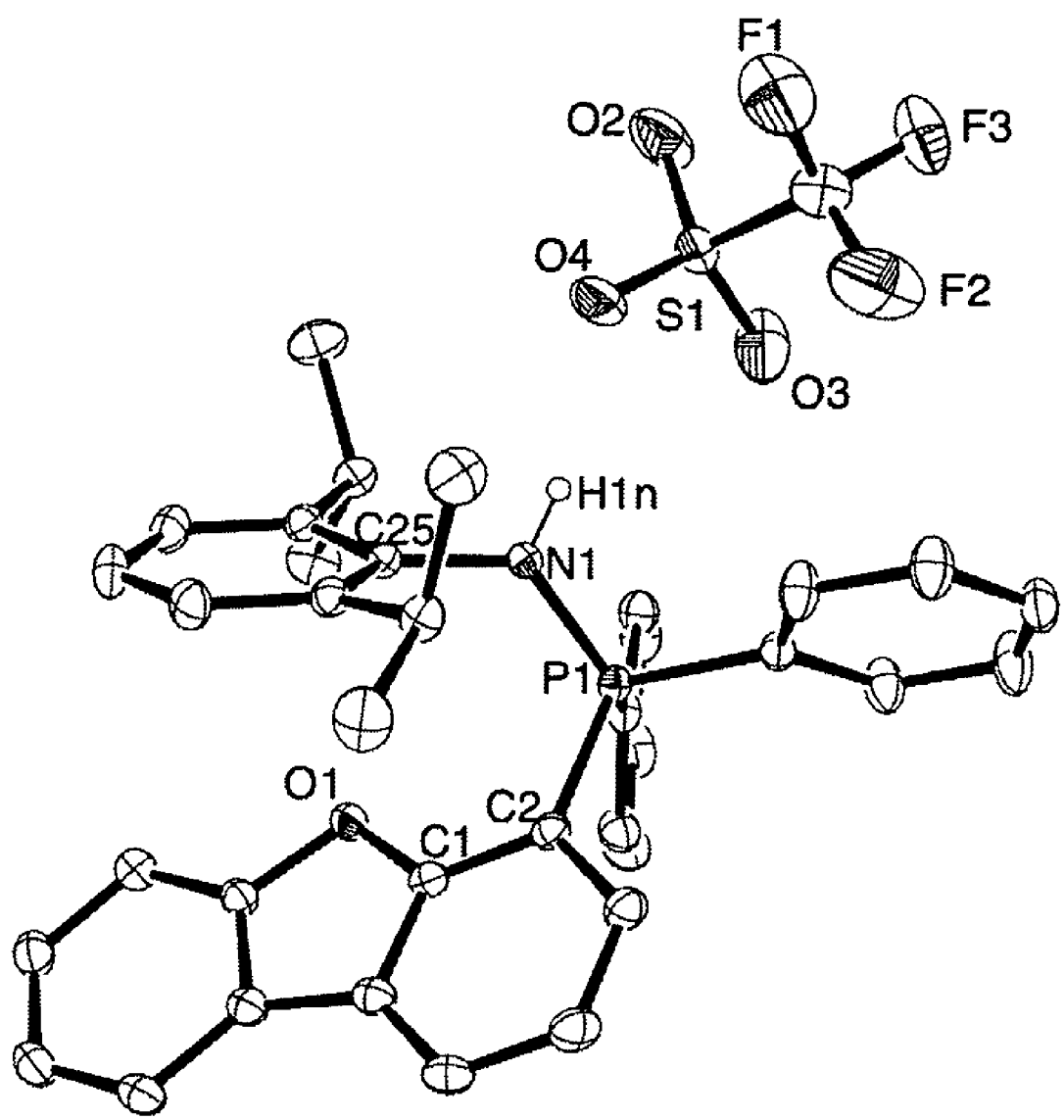
FIG. 2 shows the X-ray crystal structure of a protonated ligand according to one embodiment of the present disclosure.

As seen in FIG. 2, the x-ray crystal structure of the protonated ligand was obtained. The acidic proton was located from the electron density map and refined freely. A significant hydrogen-bonding interaction between the triflate anion and H1n is noted (N1-O4=2.789(2) Å). Further evidence for the protonation of the phosphinimine nitrogen is provided by a P—N bond (P1-N1=1.6333(15) Å) elongation of 0.07 Å, relative to that observed in the neutral structure. The torsion angles about the C—P(C1-C2-P1-N1=64.86(17)° and P—N bonds (C2-P1-N1-C25 =−4.55(17)° are both distorted from ideal chelate geometry. However, unlike the neutral analogue, the major distortion is rotation about the P—N bond, which is presumably due to the cation-anion hydrogen-bonding interaction.

Example 14

X-ray Crystallography of

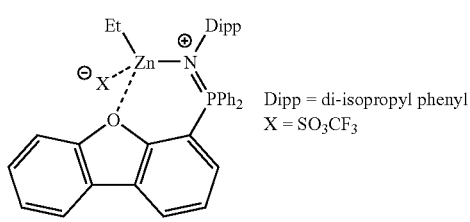

Dipp = di-isopropyl phenyl
X = SO$_3$CF$_3$

Figure 3:
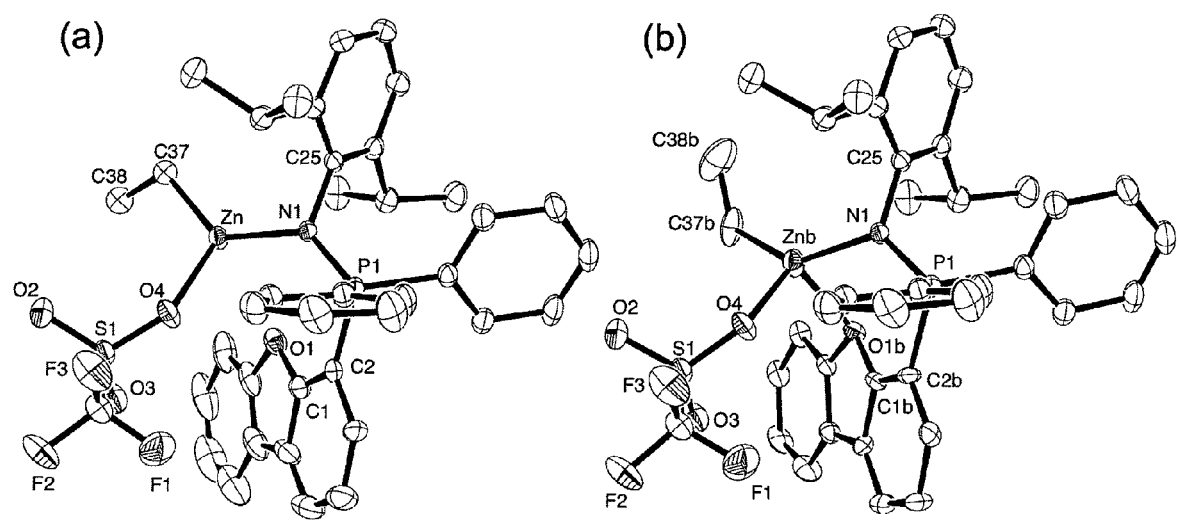
FIG. 3 shows the X-ray crystal structures of the major component (a) and the minor component (b) of a cationic divalent metal catalyst according to one embodiment of the present disclosure.

The molecular structure of the cationic divalent zinc catalyst was crystallographically established determined as seen in FIGS. 3(a) and (b).

A high degree of disorder exists in the structure necessitating the modeling of the zinc atom, the ethyl group, and the entire dbf backbone together as a 66:34 disorder over two sites. This disorder appears to result from an interplay between the steric interaction of the ethyl group and ligand versus binding strength of the zinc center and the oxygen atom of the dbf framework. The major component of the disorder has a geometry in which the ethyl group is rotated away from the Dipp group, resulting in a long Zn—O interaction (Zn—O1=2.602(10) Å). In the less abundant component, the ethyl group is rotated toward the Dipp group in a sterically less favored position, but the Zn—O bond distance is substantially shorter (Znb-O1b=2.08(2) Å). Interestingly, there is a widening of the N—Zn-Cethyl bond angle in the minor component (N—Zn—C37=131.6(2)°; N—Znb-C37b=138.8(5)°, rather than the opposite effect which would be expected from stronger coordination of the oxygen atom. This can be attributed to the enhanced steric repulsion between the ethyl and Dipp groups. These observations suggest that while the Zn—O interaction is not as strong as the Zn—N bonding, it is likely to play a key role in the chemistry of the system. For both components, torsion angles about the C—P(N1-P1-C2-C1=20.1(17)° and P—N bonds (C2-P1-N1-C25=−156.1 (6)° are close to ideal.

Example 15

X-ray Crystallography of 4,6-(MesN=PPh$_2$)$_2$ C$_{12}$H$_6$O (6a)

Figure 4:
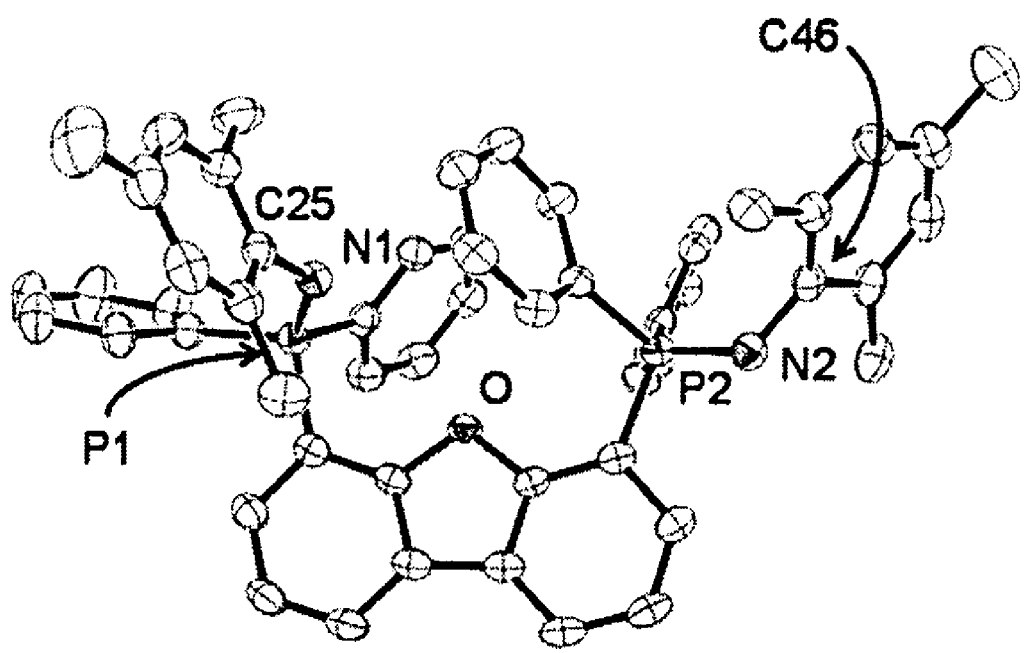

X-ray quality single crystals of the ligand were readily obtained and its molecular structure was determined crystallographically as seen in FIG. 4. Crystals of 4,6-(MesN=PPh$_2$)$_2$C$_{12}$H$_6$O were grown at ambient temperature from a saturated solution of the compound in a mixture of toluene and pentane. The reflection data were consistent with the space group P2$_1$/n. The asymmetric unit contained a single molecule of the compound and no solvent molecules. All non-hydrogen atoms in the structure are well ordered and have been modeled anisotropically. The largest residual electron density peak (0.279 e/Å$^{-3}$) is associated with a phosphorus atom. Full-matrix least squares refinement on F$^2$ gave R$_1$=0.0350 for 2σ data and wR$_2$=0.0912 for all data (GoF=1.036). Selected bond lengths (Å) and angles(°): P(1)-N(1) 1.549 (1), P(2)-N(2) 1.565(1); P(1)-N(1)-C(25) 129.5 (1), P(2)-N(2)-C(46) 122.9(1). (right). Molecular structure of 4,6-(MesN=PPh$_2$)$_2$C$_{12}$H$_6$O (30% probability ellipsoids. BPh$_4^-$, solvent (acetone), and all H atoms except N—H (calculated) omitted for clarity.) Selected bond lengths (Å) and angles (°): P(1)-N(1) 1.549 (1), P(2)-N(2) 1.565 (1); P(1)-N(1)-C(25) 129.5(1), P(2)-N(2)-C(46) 122.9(1).

Example 16

X-ray Crystallography of 4,6-(o-tolyIN=PPh$_2$)$_2$ C$_{12}$H$_6$O (6b)

Figure 5:
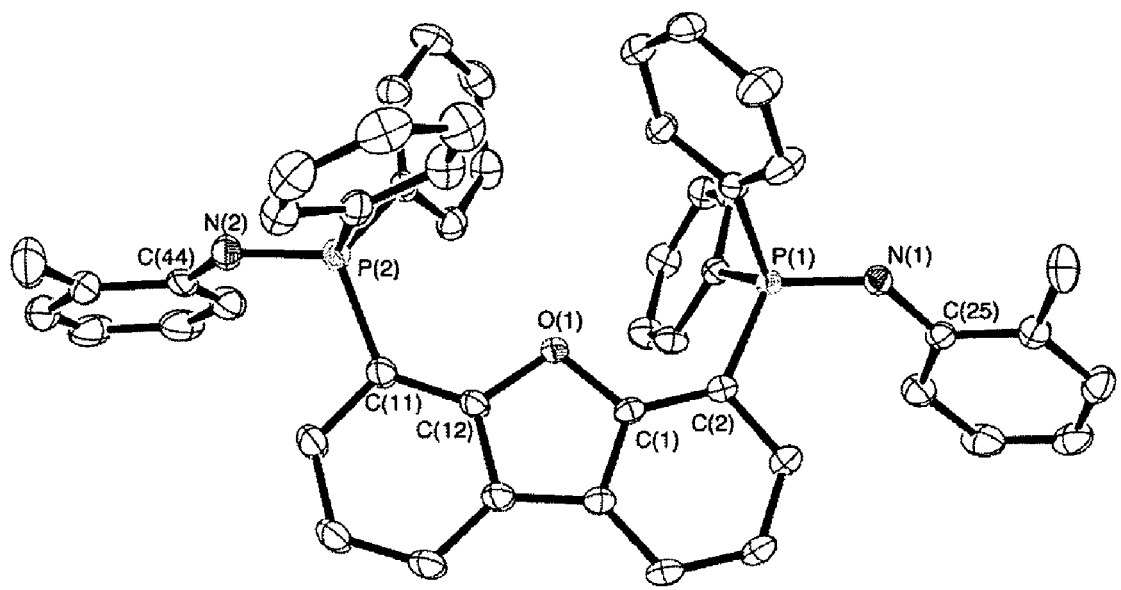
FIG. 5 shows the X-ray crystal structure of compound 6b.

X-ray quality single crystals of the ligand were readily obtained and its molecular structure was determined crystallographically as seen in FIG. 5. Crystals of 4,6-(o-tolyl-N=PPh$_2$)$_2$C$_{12}$H$_6$O were grown by slow diffusion of hexane into a methylene chloride solution of the compound at room temperature. The reflection data were consistent with the space group P2$_1$/c, and the structure was determined at a resolution of 0.84 Å. The asymmetric unit contained a single molecule of the compound. All atoms are well ordered and have been refined anisotropically. The unit cell contains total solvent accessible voids of 172 Å$^3$ (4.3% of the unit cell), and accounting for this using the SQUEEZE subroutine of the PLATON software suite gave improved residuals. A total of 13 electrons were removed, and were left unassigned. The SQUEEZE processed data were used for all subsequent refinement cycles. The largest residual electron density peak (0.533 eÅ$^{-3}$) is associated with one of the P—C$_{Ph}$ bonds. Full-matrix least squares refinement on F$^2$ gave R$_1$=0.0394 for 2σ data and wR$_2$=0.1079 for all data (GoF= 1.081). Selected bond lengths (Å), bond angles (°), and torsion angles (°): P(1)-N(1) 1.564 (1), P(2)-N(2) 1.576 (2), P(1)-C(2) 1.822 (2), P(2)-C(11) 1.817 (2), N(1)-C(25) 1.390 (2), N(2)-C(44) 1.411 (3), C(2)-P(1)-N(1) 112.14(8), P(1)-N (1)-C(25) 131.3(1), C(11)-P(2)-N(2) 111.94(8), P(2)-N(2)-C

(44) 125.8(2), N(1)-P(1)-C(2)-C(1) 172.7(1), C(2)-P(1)-N(1)-C(25) 62.2(2), N(2)-P(2)-C(11)-C(12) 173.2(2), C(11)-P(2)-N(2)C(44) −63.8(2).

Example 17

X-ray Crystallography of 4,6-(2-$^i$PrPhN=PPh$_2$)$_2$ C$_{12}$H$_6$O (6c)

Figure 6:
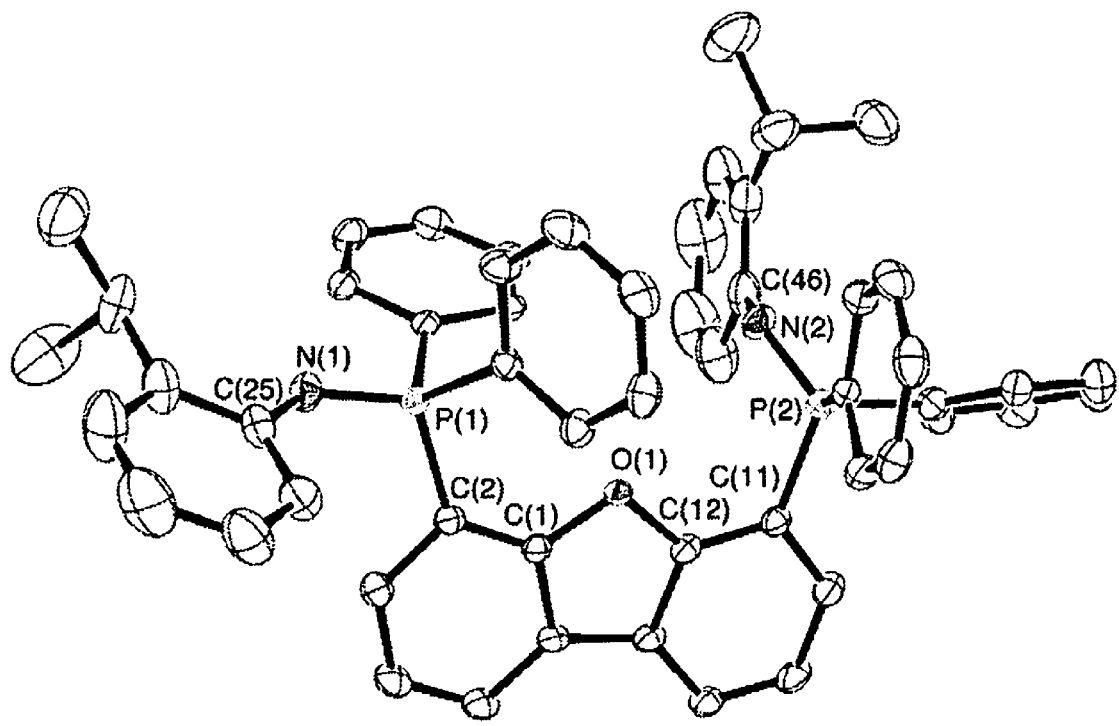
FIG. 6 shows the X-ray crystal structure of compound 6c.

X-ray quality single crystals of the ligand were readily obtained and its molecular structure was determined crystallographically as seen in FIG. 6. Crystals of 4,6-(2-$^i$PrPh-N=PPh$_2$)$_2$C$_{12}$H$_6$O were grown by slow diffusion of hexane into a methylene chloride solution of the compound at −35° C. The reflection data were consistent with the space group P(−1), and the structure was determined at a resolution of 0.84 Å. The asymmetric unit contained a single molecule of the compound. All non-solvent atoms are well ordered and have been refined anisotropically. The unit cell contains a single molecule of dichloromethane which had partially desolvated prior to placement of the crystal in the cold gas stream (20% Occupancy). The unit cell contains no solvent accessible voids. The largest residual electron density peak (0.690 eÅ$^{-3}$) is associated with the dichloromethane solvent molecule. Full-matrix least squares refinement on F$^2$ gave R$_1$=0.0646 for 2σ data and wR$_2$=0.1827 for all data (GoF=1.110). Selected bond lengths (Å), bond angles (°), and torsion angles (°): P(1)-N(1) 1.560(4), P(2)-N(2) 1.542 (3), P(1)-C(2) 1.821 (4), P(2)-C(11) 1.812(4), N(1)-C(25) 1.380 (6), N(2)-C(46) 1.380(6), C(2)-P(1)-N(1) 114.4(2), P(1)-N(1)-C(25) 129.1(3), C(11)-P(2)-N(2) 117.8(2), P(2)-N(2)-C(46) 127.5(4), N(1)-P(1)-C(2)-C(1) −179.8(3), C(2)-P(1)-N(1)-C(25) 75.2 (4), N(2)-P(2)-C(11)-C(12) −46.8(4), C(11)-P(2)-N(2)-C(46) −76.7(5).

Example 18

X-ray Crystallography of 4,6-(4-$^i$PrPhN=PPh$_2$)$_2$ C$_{12}$H$_6$O (6d)

Figure 7:
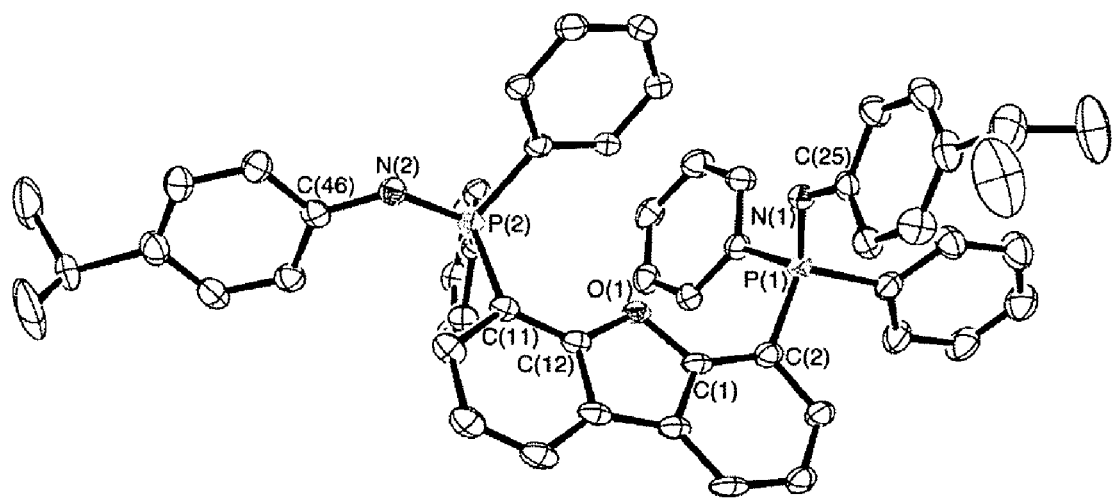
FIG. 7 shows the X-ray crystal structure of compound 6d.

X-ray quality single crystals of the ligand were readily obtained and its molecular structure was determined crystallographically as seen in FIG. 7. Crystals of 4,6-(4-$^i$PrPh-N=PPh$_2$)$_2$C$_{12}$H$_6$O were grown from a solution of the compound in a mixture of pentane and methylene chloride at −35° C. The reflection data were consistent with the orthorhombic space group Pca2$_1$, and the structure was determined at a resolution of 0.84 Å. The asymmetric unit contained a single molecule of the compound in addition to a single molecule of pentane. One of the isopropyl groups is disordered over two sites, at an approximate 60:40 ratio. The unit cell contains total solvent accessible voids of 396 Å$^3$, which have been accounted for using the SQUEEZE subroutine of the PLATON software suite. A total of only 24 electrons were removed (3 electrons per asymmetric unit), and have been left unassigned. The largest residual electron density peak (0.265 eÅ$^{-3}$) is associated with one of the P—C$_{Ph}$ bonds. Full-matrix least squares refinement on F$^2$ gave R$_1$=0.0517 for 2σ data and wR$_2$=0.1238 for all data (GoF=1.106). Selected bond lengths (Å), bond angles (°), and torsion angles (°): P(1)-N(1) 1.560(3), P(2)-N(2) 1.558 (3), P(1)-C(2) 1.817(3), P(2)-C(11) 1.831 (3), N(1)-C(25) 1.392 (4), N(2)-C(46) 1.383 (4), C(2)-P(1)-N(1) 116.2(2), P(1)-N(1)-C(25) 127.3(2), C(11)-P(2)-N(2) 113.2(1), P(2)-N(2)-C(46) 134.5(2), N(1)-P(1)-C(2)-C(1) 58.5 (3), C(2)-P(1)-N(1)-C(25) 62.4 (3), N(2)-P(2)-C(11)-C(12) −169.2(2), C(11)-P(2)-N(2)-C(46) −75.5(3).

Example 19

X-ray Crystallography of 4,6-(PhN=PPh$_2$)$_2$ C$_{12}$H$_6$O (6e)

Figure 8:
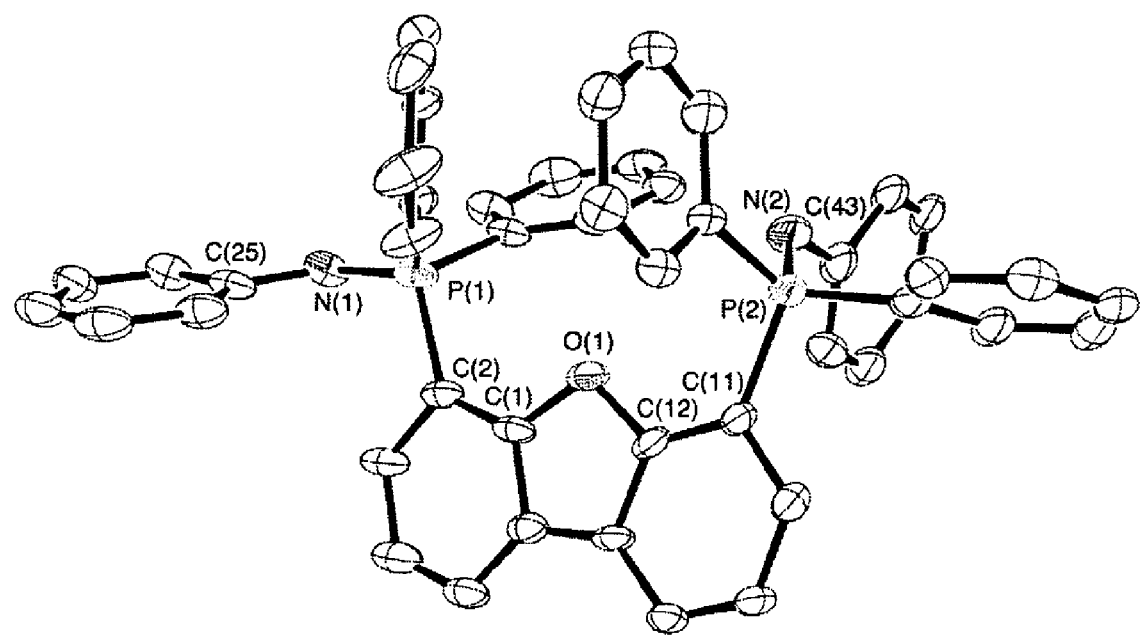
FIG. 8 shows the X-ray crystal structure of compound 6e.

X-ray quality single crystals of the ligand were readily obtained and its molecular structure was determined crystallographically as seen in FIG. 8. Crystals of 4,6-(Ph-N=PPh$_2$)$_2$C$_{12}$H$_6$O were grown as colourless needles from a concentrated benzene solution of the compound at room temperature. The reflection data were consistent with the space group P(−1). The structure was determined at a resolution of 1.0 Å due to low intensity of the high angle data. All atoms are well ordered and have been refined anisotropically. The unit cell contains total solvent accessible voids of 354 Å$^3$ (15.8% of the unit cell), which was accounted for using the SQUEEZE subroutine of the PLATON software suite. A total of 112 electrons were removed, which are assigned to 2.67 molecules of benzene (1.33 molecules of benzene per asymmetric unit). The largest residual electron density peak (0.215 eÅ$^{-3}$) is associated with the dibenzofuran moiety. Full-matrix least squares refinement on F$^2$ gave R$_1$=0.0640 for 26 data and wR$_2$=0.1412 for all data (GoF=1.045).). Selected bond lengths (Å), bond angles (°), and torsion angles (°): P(1)-N(1) 1.584(5), P(2)-N(2) 1.555 (6), P(1)-C(2) 1.816 (6), P(2)-C(11) 1.836 (6), N(1)-C(25) 1.430(6), N(2)-C(43) 1.421 (7), C(2)-P(1)-N(1) 111.9(3), P(1)-N(1)-C(25) 127.2(3), C(11)-P(2)-N(2) 118.5(3), P(2)-N(2)-C(43) 125.6(4), N(1)-P(1)-C(2)-C(1) −175.6(5), C(2)-P(1)-N(1)-C(25) 69.6 (5), N(2)-P(2)-C(11)-C(12)-49.5(6), C(11)-P(2)-N(2)-C(43)-59.6(6).

Example 20

X-ray Crystallography of [H$_2$-4,6-(MesN=PPh$_2$)$_2$ C$_{12}$H$_6$O][B(C$_6$H$_5$)$_4$]$_2$ (8)

Figure 9:
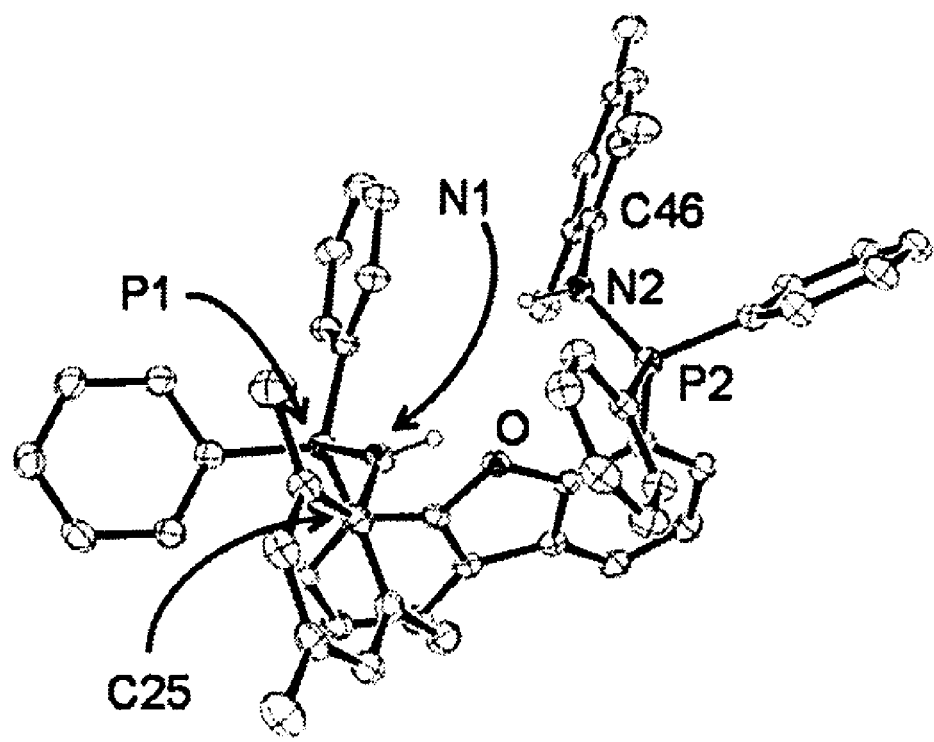
FIG. 9 shows the X-ray crystal structure of compound 8.

X-ray quality single crystals of the ligand were readily obtained and its molecular structure was determined crystallographically as seen in FIG. 9. Crystals of [H$_2$-4,6-(MesN=PPh$_2$)$_2$C$_{12}$H$_6$O][B(C$_6$H$_5$)$_4$]$_2$ were grown by slow evaporation of an acetone solution of the compound. The reflection data were consistent with the orthorhombic space group Pbca. The asymmetric unit contained half of a molecule of the compound in addition to half of a molecule of acetone, both of which occupied a site of symmetry. All non-hydrogen atoms in the structure are well ordered and have been modeled anisotropically. The largest residual electron density peak (0.196 e/Å$^{-3}$) is associated with the phosphorus atom. Full-matrix least squares refinement on F$^2$ gave R$_1$=0.0466 for 20 data and wR$_2$=0.1183 for all data (GoF=1.028). Selected bond lengths (Å) and angles (°): P(1)-N(1) 1.639 (2), N(1)-H(1N) 0.894 (2); P(1)-N(1)-C(25) 125.6 (1).

Example 21

X-ray Crystallography of [4,6-(MesN=PPh$_2$)$_2$ C$_{12}$H$_6$O.MgBu][BPh$_4$] (9a)

Figure 10:
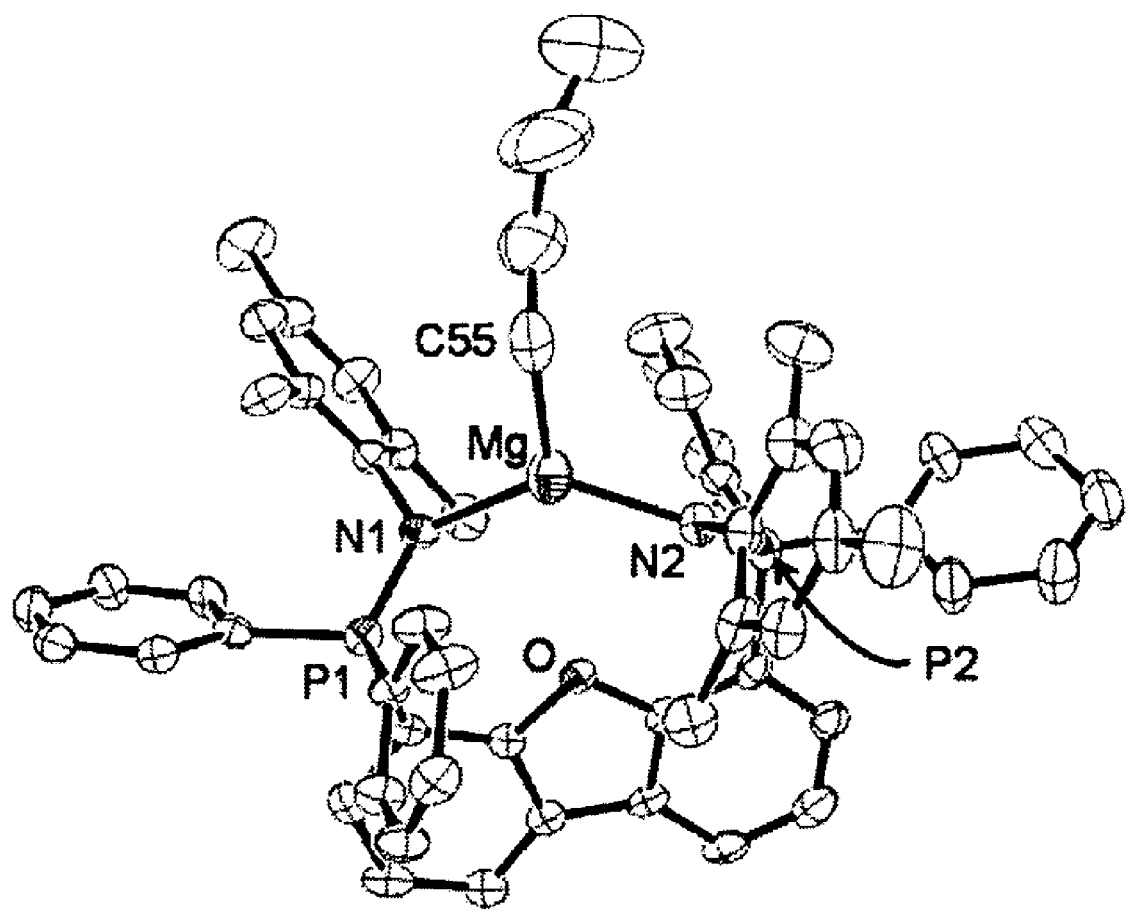

X-ray quality single crystals of the ligand were readily obtained and its molecular structure was determined crystallographically as seen in FIG. 10. Crystals of [4,6-(MesN=PPh$_2$)$_2$C$_{12}$H$_6$O.MgBu][BPh$_4$] were grown by slow diffusion of heptane into a benzene solution of the compound. The reflection data were consistent with the monoclinic space group P2$_1$/c. The asymmetric unit contained a single molecule of the compound. Guest solvent molecules were poorly ordered, giving rise to an elevated residual electron density. This problem is compounded by the poor scattering ability of the small plate crystals, which did not generate high angle data (>1 Å) of sufficient quality. Accounting for the disordered solvent using the SQUEEZE subroutine of the PLATON software suite gave a reduced residual electron density. A total of 184 electrons were removed from a volume of 1133 Å$^3$ (15.2% of the unit cell), and are assigned to 3.2 molecules of heptane (This equates to 0.8 heptane molecules per asymmetric unit). The SQUEEZE processed data were used for all subsequent refinement cycles. All non-hydrogen atoms were well ordered and refined anisotropically. The largest residual electron density peak (0.478 e/Å$^{-3}$) is associated with the magnesium atom. Full-matrix least squares refinement on F$^2$ gave R$_1$=0.0772 for 2σ data and wR$_2$=0.2121 for all data (GoF=1.038). Metrical parameters are given below for the structure both before and after being SQUEEZED. Selected bond lengths (Å) and angles (°): P(1)-N(1) 1.602 (5), P(2)-N(2) 1.601 (5), Mg—N(1) 2.086 (6), Mg—N(2) 2.077(5), Mg—C(55) 2.13 (1); P(1)-N(1)-Mg 129.6(3), P(2)-N(2)-Mg 130.7(3), N(1)-Mg—N(2) 132.6(2), N(1)-Mg—C(55) 115.0 (3), N(2)-Mg—C(55) 112.3(3).

Example 22

Figure 11:
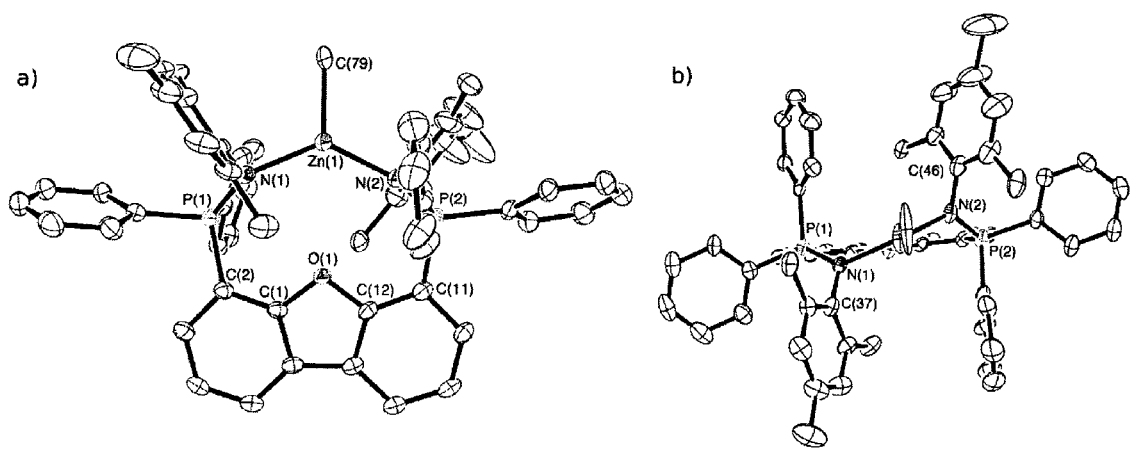
FIG. 11 shows the X-ray crystal structure of [4,6-(Mes-NPPh$_2$)$_2$C$_{12}$H$_6$O.ZnMe]⁺[BPh$_4$]⁻.

X-ray Crystallography of [4,6-(Mes-NPPh$_2$)$_2$C$_{12}$H$_6$O.ZnMe]$^+$[BPh$_4$]$^-$ X-ray quality single crystals of the ligand were readily obtained and its molecular structure was determined crystallographically as seen in FIG. 11. Crystals of [4,6-(Mes-NPPh$_2$)$_2$C$_{12}$H$_6$O.ZnMe]$^+$[BPh$_4$]$^-$ (prepared using a method analogous to that used for 9a) were grown by slow cooling of a solution of the compound in a mixture of benzene and bromobenzene from 70° C. to ambient temperature. The reflection data were consistent with the space group P(–1), and the structure was determined at a resolution of 0.84 Å. The asymmetric unit contained a single molecule of the compound. Most atoms are well ordered, with the exception of the methyl group on the zinc centre, which is disordered over two sites at a ratio of 70:30, and the nearest neighboring phenyl ring of the tetraphenylborate anion, which exhibits a concomitant two site disorder. The unit cell contains total solvent accessible voids of 255 Å$^3$ (7.6% of the unit cell), and accounting for this using the SQUEEZE™ subroutine of the PLATON™ software suite gave improved residuals. A total of 37 electrons were removed, and are assigned to 0.88 molecules of benzene (0.44 per molecules of benzene per asymmetric unit). The SQUEEZE™ processed data were used for all subsequent refinement cycles. The largest residual electron density peak (0.557 eÅ$^{-3}$) is associated with the disordered methyl group. Full-matrix least squares refinement on F$^2$ gave R$_1$=0.0656 for 2σ data and wR$_2$=0.1777 for all data (GoF=1.021). Selected bond lengths (Å) and angles (°): Zn(1)-N(1) 2.046 (3), Zn(1)-N(2) 2.034(3), Zn(1)-C(79) 2.045 (9), P(1)-N(1) 1.609 (3), P(2)-N(2) 1.603 (3); N(1)-Zn(1)-C(79) 114.3(2), N(2)-Zn(1)-C(79) 113.5(3), N(1)-Zn(1)-N(2) 131.8(1), P(1)-N(1)-Zn(1) 131.0(2), C(37)-N(1)-Zn(1) 110.2(2), P(1)-N(1)-C(37) 118.7(2), P(2)-N(2)-Zn(1) 127.1(2), C(46)-N(2)-Zn(1) 114.5(2), P(2)-N(2)-C(46) 118.4(3).

Example 23

X-ray Crystallography of [4,6-(Mes-NPPh$_2$)$_2$C$_{12}$H$_6$O.ZnOAc]$^+$[BPh$_4$]$^-$ (9d)

Figure 12:
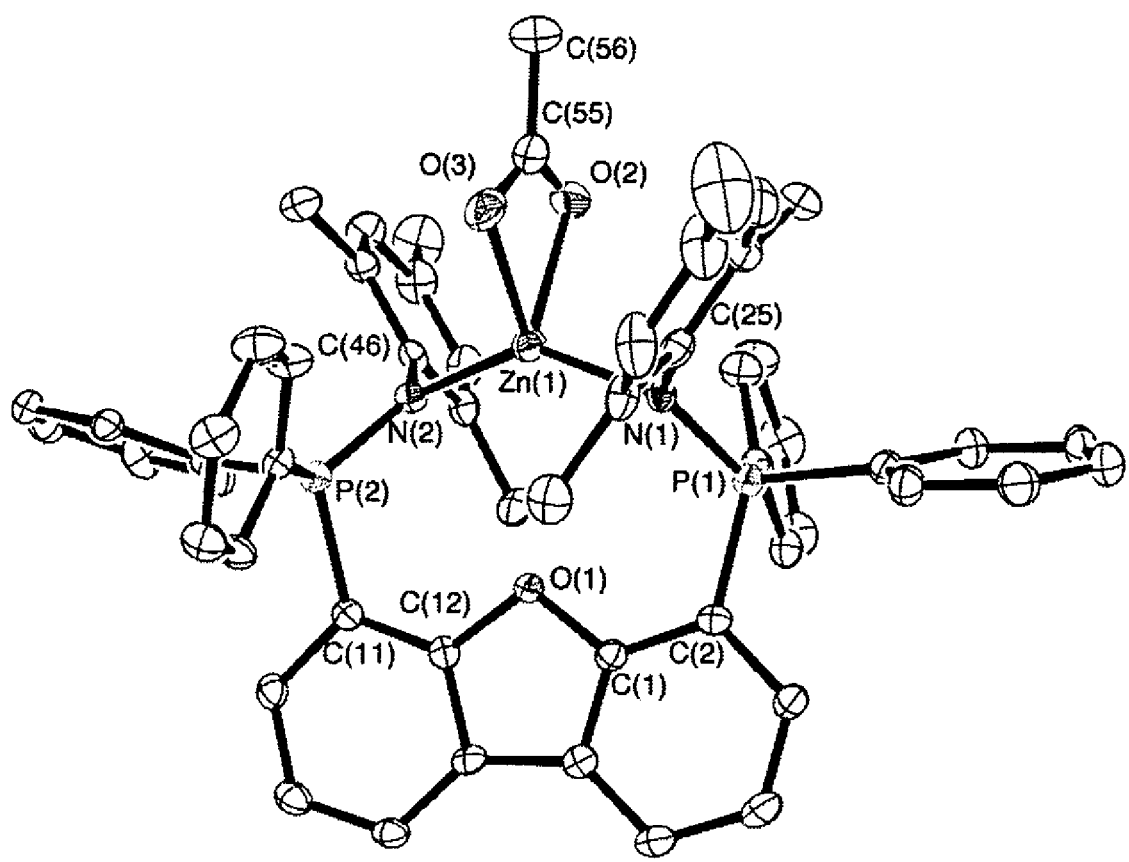
FIG. 12 shows the X-ray crystal structure of compound 9d.

X-ray quality single crystals of the ligand were readily obtained and its molecular structure was determined crystallographically as seen in FIG. 12. Crystals of [4,6-(Mes-NPPh$_2$)$_2$C$_{12}$H$_6$O.ZnOAc]$^+$[BPh$_4$]$^-$ were grown by slow cooling a solution of the compound in a benzene/bromobenzene mixture from 100° C. to ambient temperature. The reflection data were consistent with the space group P2(1)/c, and was determined at a resolution of 0.84 Å. The asymmetric unit contained a single molecule of the compound. All non-solvent atoms in the unit cell are well ordered and have been refined anisotropically. Solvent accessible voids in the unit cell were accounted for using the SQUEEZE subroutine of the PLATON software suite, giving improved residuals. A total of 160 electrons were removed from a volume of 986 Å$^3$ (13.1% of the unit cell). These electrons have been assigned to 3.8 molecules of benzene (0.95 molecules of benzene per asymmetric unit). SQUEEZE processed data were used for all subsequent refinement cycles. The largest residual electron density peak (0.880 eÅ$^{-3}$) is associated with a molecule of benzene. Full-matrix least squares refinement on F$^2$ gave R$_1$=0.0620 for 2σ data and wR$_2$=0.1544 for all data (GoF=1.019). Selected bond lengths (Å) and angles (°): Zn(1)-N(1) 1.972 (3), Zn(1)-N(2) 1.971 (3), Zn(1)-O(2) 2.089 (3), Zn(1)-O(3) 2.082 (3), P(1)-N(1) 1.606 (3), P(2)-N(2) 1.614 (3); N(1)-Zn(1)-O(2) 104.8(1), N(1)-Zn(1)-O(3) 102.0(1), N(2)-Zn(1)-O(2) 106.1(1), N(2)-Zn(1)-O(3) 111.5 (1), N(1)-Zn(1)-N(2) 141.7(1), O(2)-Zn(1)-O(3) 63.8 (2), P(1)-N(1)-Zn(1) 128.2(2), C(25)-N(1)-Zn(1) 113.1(2), P(1)-N(1)-C(25) 118.6(2), P(2)-N(2)-Zn(1) 127.7(2), C(46)-N(2)-Zn(1) 113.4(2), P(2)-N(2)-C(46) 119.0(2).

FULL CITATIONS FOR DOCUMENTS REFERRED TO IN THE SPECIFICATION (1) For general reviews see: (a) O'Keefe, B. J.; Hillmyer, M. A.; Tolman, W. B. *J. Chem. Soc., Dalton Trans.* 2001, 2215-2224.
  (b) Wu, J.; Yu, T.-L; Chen, C.-T.; Lin C.-C. *Coord. Chem. Rev.* 2006, 250, 602-626.
  (c) Platel, R. H.; Hodgson, L. M.; Williams, C. K. *Polym. Rev.* 2008, 48, 11-63.
(2) (a) Cheng, M.; Attygalle, A. B.; Lobkovsky, E. B.; Coates, G. W. *J. Am. Chem. Soc.* 1999, 121, 11583-11584.
  (b) Chisholm, M. H.; Eilerts, N. W.; Huffman, J. C.; Iyer, S. S.; Pacold, M.; Phomphrai, K. *J. Am. Chem. Soc.* 2000, 122, 11845-11854.
  (c) Williams, C. K.; Breyfogle, L. E.; Choi, S. K.; Nam, W.; Young, V. G., Jr.; Hillmyer, M. A.; Tolman, W. B. *J. Am. Chem. Soc.* 2003, 125, 11350-11359.
  (d) Hill, M. S.; Hitchcock, P. B. *J. Chem. Soc., Dalton. Trans.* 2002, 4694-4702.
  (e) Lian, B.; Thomas, C. M.; Casagrande, O. L., Jr.; Lehmann, C. W.; Roisnel, T.; Carpentier, J.-F. *Inorg. Chem.* 2007, 46, 328-340.
  (f) Alonso-Moreno, C.; Garcés, A.; Sànchez-Barba, L.-F.; Fajardo, M.; Fernández-Baeza, J.; Otero, A.; Lara-Sánchez, A.; Antiñolo, A.; Broomfield, L.; López-Solera, M. I.; Rodríguez, A. M. *Organometallics* 2008, 27, 1310-1321.
  (g) Chen, H.-Y.; Tang, H.-Y.; Lin, C.-C. *Macromolecules* 2006, 39, 3745-3752.
(3) (a) Jensen, T. R.; Breyfogle, L. E.; Hillmyer, M. A.; Tolman, W. B. *Chem. Commun.* 2004, 2504-2505.
  (b) Boerner, J.; Herres-Pawlis, S.; Fluorke, U.; Huber, K. *Eur. J. Inorg. Chem.* 2007, 5645-5651.
  (c) Jeong, J. H.; An, Y. H.; Kang, Y. K.; Nguyen, Q. T.; Lee, H.; Novak, B. M. *Polyhedron* 2008, 27, 319-324.
(4) (a) Sarazin, Y.; Schormann, M.; Bochmann, M. *Organometallics* 2004, 23, 3296-3302.

(b) Samantaray, M. K.; Katiyar V.; Roy D.; Pang K.; Nanavati H.; Stephen R.; Sunoj R. B.; Ghosh P. *Eur. J. Inorg. Chem.* 2006, 2975-2984.

(c) Dagorne, S.; Le Bideau, F.; Welter, R.; Bellemin-Laponnaz, S.; Maisse-Francoise, A. *Chem. Eur. J.* 2007, 13, 3202-3217.

(5) Haenel, M. W.; Jakubik, D.; Rothenberger, E.; Schroth, G. *Chem. Ber.* 1991, 124, 1705-1710.

(6) (a) Meyer, J.; Staudinger, H. *Helv. Chim. Acta* 1919, 2, 635-646.

(b) Alajarin, M.; Lopez-Leonardo, C. L.; Llamas-Lorente, P. L.; Bautista, D. *Synthesis* 2000, 14, 2085-2091.

(7) Kranenburg, M.; van der Burgt, Y. E. M.; Kamer, P. C. J.; van Leeuwen, P. W. N. M.; Goubitz, K.; Fraanje, J. *Organometallics* 1995, 14, 3081-3089.

(8) Murata, S.; Abe, S.; Tomioka, H. *J. Org. Chem.* 1997, 62, 3055-3061.

(9) Sheldrick, G. M.; *Acta. Cryst.* 2008, A64, 112-112.

We claim:

1. A catalyst for cyclic lactone polymerization of the formula I:

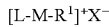   (I)

wherein
L is a neutral ancillary ligand of the formula (V)

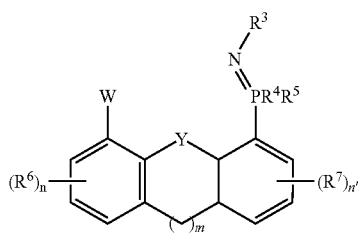   (V)

Y is O or S;

$R^3$ is selected from $C_{1-20}$alkyl, $C_{3-20}$cycloalkyl, $C_{6-14}$aryl and $Si(R^c)_3$, said latter 4 groups being optionally substituted with one or more substituents independently selected from $C_{1-6}$alkyl, fluoro-substituted $C_{1-6}$alkyl, phenyl, phenyl substituted with one to five $C_{1-6}$alkyl, and halo, and $R^c$ is selected from $C_{1-20}$alkyl, fluoro-substituted $C_{1-20}$alkyl, $C_{3-20}$cycloalkyl and $C_{6-14}$aryl;

$R^4$ and $R^5$ are simultaneously or independently selected from $C_{1-20}$alkyl, $C_{3-20}$cycloalkyl and $C_{6-14}$aryl, said latter 3 groups being optionally substituted with one or more substituents independently selected from $C_{1-6}$alkyl, fluoro-substituted $C_{1-6}$alkyl and halo;

$R^6$ and $R^7$ are simultaneously or independently selected from $C_{1-6}$alkyl, fluoro-substituted $C_{1-6}$alkyl and halo;

W is H, a chiral group or $-P(R^8R^9)=N-R^{10}$, $R^8$, $R^9$ and $R^{10}$ are as defined for $R^4$, $R^5$ and $R^3$, respectively;

m is 0, 1 or 2; and when m is 0, the ligand of formula (V) comprises a dibenzofuran or dibenzothiophene fused ring system;

n and n' are simultaneously or independently 0, 1, 2 or 3,

M is a divalent metal suitable for cyclic lactone polymerization;

$R^1$ is selected from halo, $R^a$, $OR^a$, $C(O)R^a$, $C(O)OR^a$, $OC(O)R^a$, $C(O)NR^aR^b$ and $NR^aR^b$, $R^a$ and $R^b$ are simultaneously or independently selected from H, $C_{1-10}$alkyl, fluoro-substituted $C_{1-10}$alkyl and $C_{6-14}$aryl, wherein $C_{6-14}$aryl is unsubstituted or substituted with one or more substituents independently selected from halo, $C_{1-6}$alkyl, $NR^dR^e$, $OR^d$ and phenyl;

$R^d$ and $R^e$ are sumultaneously or independently selected from H, $C_{1-10}$alkyl, fluoro-substituted $C_{1-10}$alkyl and $C_{6-14}$aryl; and $X^-$ is a suitable non- or weakly-coordinating anion.

2. The catalyst of claim 1, wherein Y is O.

3. The catalyst of claim 1, wherein $R^3$ is selected from $C_{1-10}$alkyl, $C_{3-10}$cycloalkyl, phenyl, naphthyl, and $Si(R^c)_3$, said latter 5 groups being optionally substituted, and $R^c$ is selected from $C_{1-10}$alkyl, fluoro-substituted $C_{1-10}$alkyl, $C_{3-10}$cycloalkyl, phenyl and naphthyl.

4. The catalyst of claim 3, wherein $R^3$ is optionally substituted phenyl, and the optional substituents are selected from $C_{1-4}$alkyl, fluoro-substituted $C_{1-4}$alkyl, phenyl, phenyl substituted with one to three $C_{1-4}$alkyl and halo.

5. The catalyst of claim 4, wherein $R^3$ is optionally substituted phenyl, and the optional substituents are selected from $C_{1-4}$alkyl.

6. The catalyst of claim 5, wherein $R^3$ is

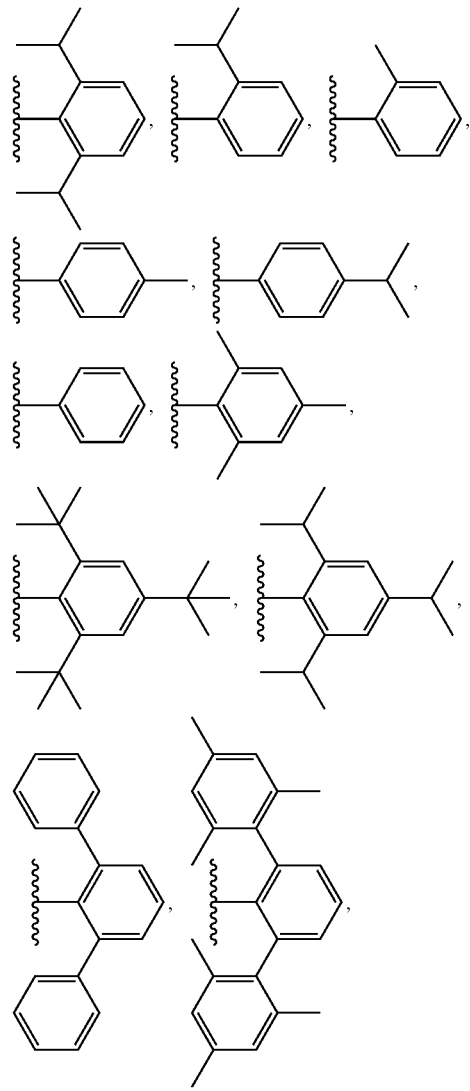

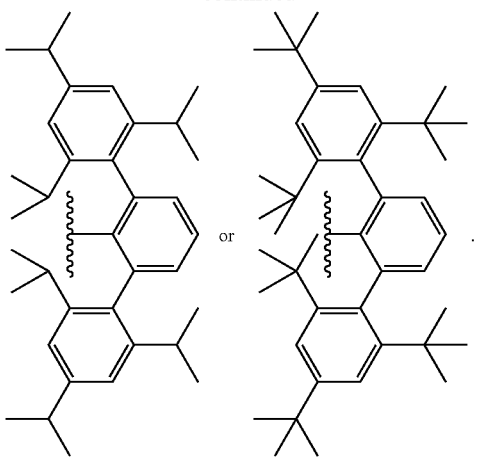

7. The catalyst of claim 1, wherein $R^4$ and $R^5$ are simultaneously selected from $C_{1-6}$alkyl and phenyl, said latter 2 groups being optionally substituted with one or more substituents independently selected from $C_{1-6}$alkyl, fluoro-substituted $C_{1-6}$alkyl and halo.

8. The catalyst of claim 7, wherein $R^4$ and $R^5$ are both unsubstituted phenyl.

9. The catalyst of claim 1, wherein $R^6$ and $R^7$ are simultaneously or independently selected from $C_{1-4}$alkyl, fluoro-substituted $C_{1-6}$alkyl and halo.

10. The catalyst of claim 1, wherein W is H.

11. The catalyst of claim 1, wherein W is —P($R^8R^9$)=N—$R^{10}$.

12. The catalyst of claim 11, wherein $R^{10}$ is optionally substituted phenyl, and the optional substituents are selected from $C_{1-4}$alkyl, fluoro-substituted $C_{1-4}$alkyl, phenyl, phenyl substituted with one to three $C_{1-4}$alkyl, and halo.

13. The catalyst of claim 12, wherein $R^{10}$ is optionally substituted phenyl, wherein the optional substituents are selected from $C_{1-4}$alkyl.

14. The catalyst of claim 13, wherein $R^{10}$ is

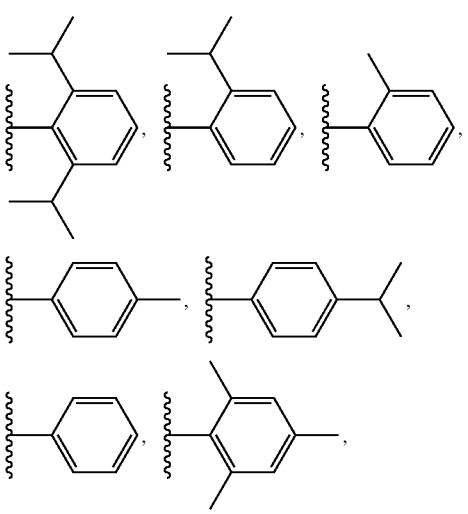

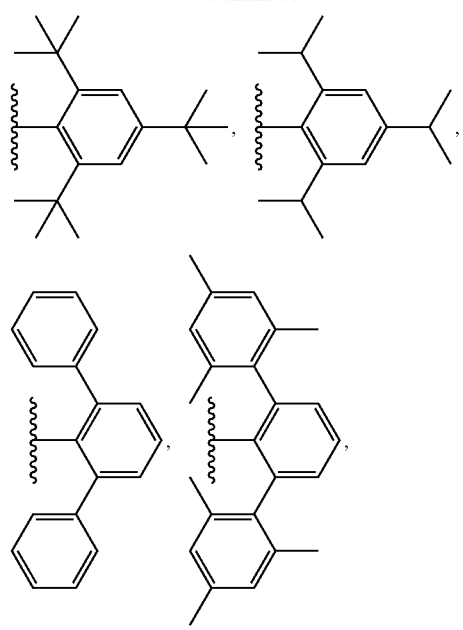

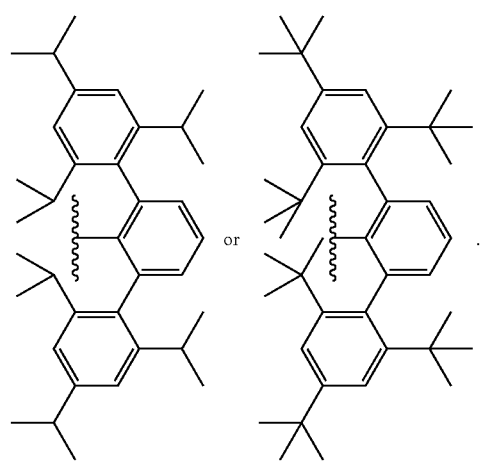

15. The catalyst of claim 11, wherein $R^8$ and $R^9$ are simultaneously selected from $C_{1-6}$alkyl and phenyl, said latter 2 groups being optionally substituted with one or more substituents independently selected from $C_{1-6}$alkyl, fluoro-substituted $C_{1-6}$alkyl and halo.

16. The catalyst of claim 15, wherein $R^8$ and $R^9$ are both unsubstituted phenyl.

17. The catalyst of claim 1, wherein W is a chiral group.

18. The catalyst of claim 17, wherein the chiral group is menthol, binaphthyl, camphor,

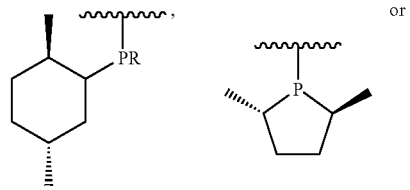

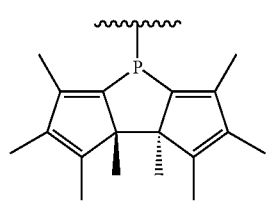

19. The catalyst of claim 1, wherein m, n and n' are all 0.

20. The catalyst according claim 1, wherein the neutral ancillary ligand is

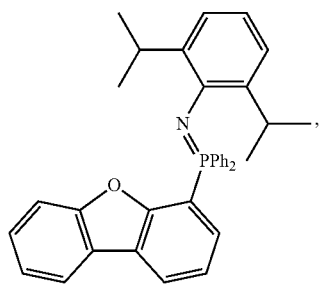
(2)

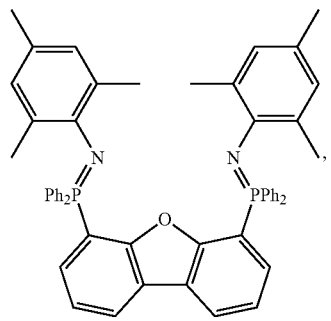
(6a)

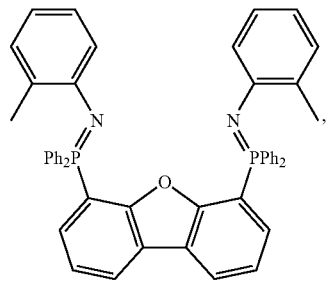
(6b)

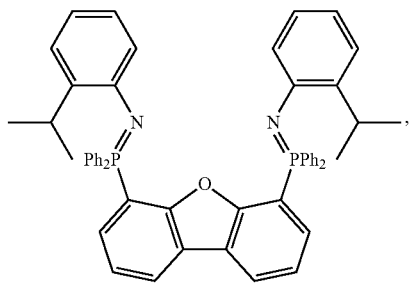
(6c)

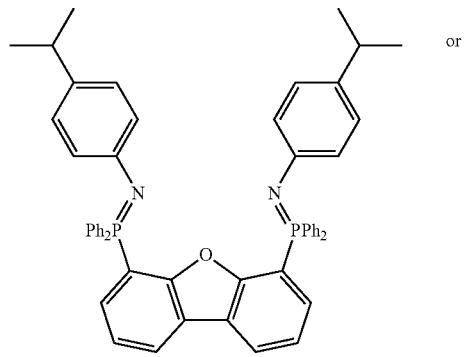
(6d)

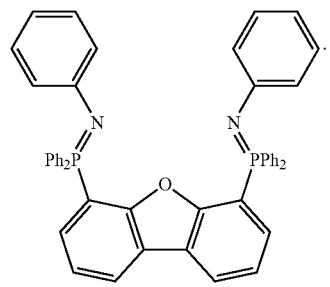
(6e)

21. The catalyst of claim 1, wherein M is $Ca^{2+}$, $Mg^{2+}$ or $Zn^{2+}$.

22. The catalyst of claim 1, wherein $R^1$ is selected from Cl, $C_{1-10}$alkyl, $C_{1-10}$alkoxide, phenyl and $NR^aR^b$, said latter 4 groups being optionally substituted with one or more substituents independently selected from $C_{1-4}$alkyl, fluoro-substituted $C_{1-4}$alkyl and F, and $R^a$ and $R^b$ are simultaneously or independently selected from H, $C_{1-10}$alkyl, fluoro-substituted $C_{1-10}$alkyl and phenyl, where $R^a$ and $R^b$ are not simultaneously H.

23. The catalyst of claim 1, wherein X– is selected from $[B(C_6F_5)_4]^-$, $[B(C_6H_5)_4]^{31}$, $[B(3,5-(CF_3)_2C_6H_3)_4]^-$ and $[SO_3CF_3]^-$.

24. The catalyst of claim 1, wherein the catalyst of formula I is

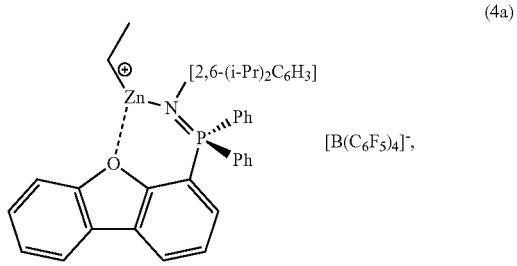
(4a)

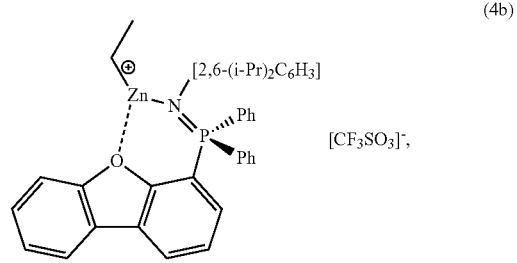
(4b)

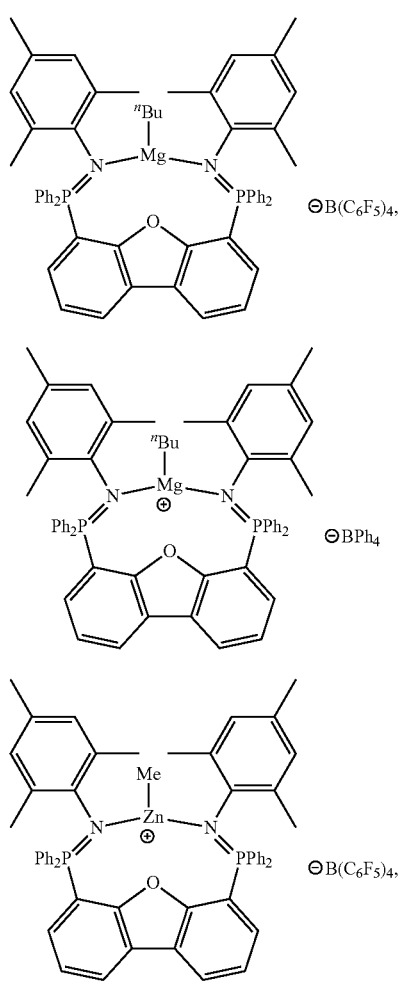

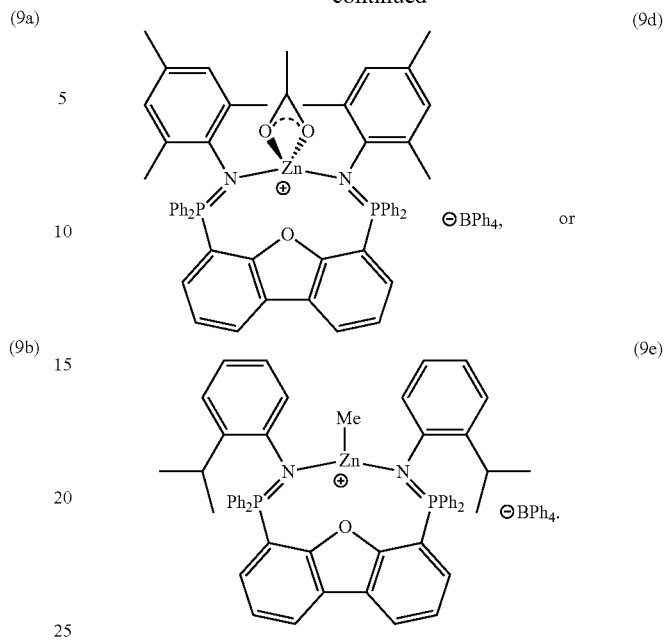

25. A method for the polymerization of one or more cyclic lactones comprising contacting the one or more cyclic lactones with a divalent metal catalyst of the formula I as defined in claim 1 under conditions for the polymerization of the cyclic lactone.

26. The method of claim 25, wherein the cyclic lactone is lactide, glycolide, ε-caprolactone, dioxanone, 1,4-dioxane-2, 3-dione, beta-propiolactone, tetramethyl glycolide, beta-butyrolactone, gammabutyrolactone, pivalolactone, trimethylene carbonate or 2,2-dimethyl trimethylene carbonate.

27. The method of claim 26, wherein cyclic lactone is lactide or ε-caprolactone.

* * * * *

UNITED STATES PATENT AND TRADEMARK OFFICE
CERTIFICATE OF CORRECTION

PATENT NO.      : 8,193,112 B2
APPLICATION NO. : 12/624936
DATED           : June 5, 2012
INVENTOR(S)     : Paul G. Hayes et al.

It is certified that error appears in the above-identified patent and that said Letters Patent is hereby corrected as shown below:

Column 44, line 39, "X-", should read --$X^-$--.

Column 44, line 40, "$[B(C_6H_5)_4]^{31}$", should read --$[B(C_6H_5)_4]^-$--.

Signed and Sealed this
Twenty-seventh Day of November, 2012

David J. Kappos
*Director of the United States Patent and Trademark Office*